US006649371B1

(12) United States Patent
Jentsch

(10) Patent No.: US 6,649,371 B1
(45) Date of Patent: Nov. 18, 2003

(54) POTASSIUM CHANNEL KCNQ5 AND SEQUENCES ENCODING THE SAME

(75) Inventor: Thomas J. Jentsch, Hamburg (DE)

(73) Assignee: NeuroSearch A/S, Ballerup (DK)

( * ) Notice: Subject to any disclaimer, the term of this patent is extended or adjusted under 35 U.S.C. 154(b) by 0 days.

(21) Appl. No.: 09/590,304

(22) Filed: Jun. 9, 2000

Related U.S. Application Data

(60) Provisional application No. 60/139,891, filed on Jun. 22, 1999.

(30) Foreign Application Priority Data

Jun. 11, 1999 (DK) ................................................ 00828

(51) Int. Cl.[7] ........................... C12P 21/06; C12N 1/20; C12N 15/74; C07H 21/04
(52) U.S. Cl. ................ 435/69.1; 435/252.3; 435/320.1; 536/23.1
(58) Field of Search ........................ 536/23.1; 435/69.1, 435/325, 252.3, 320.1

(56) References Cited

FOREIGN PATENT DOCUMENTS

| WO | WO9907832 | | 2/1999 |
|---|---|---|---|
| WO | WO9921875 | | 5/1999 |
| WO | WO9931232 | | 6/1999 |
| WO | WO/0044786 | * | 8/2000 |
| WO | WO/0061606 | * | 10/2000 |
| WO | 01/70759 A1 | | 9/2001 |
| WO | 01/70811 A1 | | 9/2001 |
| WO | 01/92526 A1 | | 12/2001 |

OTHER PUBLICATIONS

Skolnick et al., Trends in Biotech., 18(1):34–39, 2000.*
Jobling et al., Mol. Microbiol., 1991, 5(7):1755–67.*
Sambrook et al., Cold Spring Harbor Labs, 1989, pp. 9.47–9.51 and 11.48–11.49.*
Christian Biervert et al., Jan. 16, 1998 vol. 279, pp. 403–406 Science.

Q. Wang et al., Jan., 1996 vol. 12, pp. 17–23 Nature Genetics.

Björn C. Schroeder et al., Dec. 17, 1998 vol. 396 pp. 687–690 Nature.

Christian Kubisch et al., Feb. 5, 1999 vol. 96 pp. 437–446 Cell.

Schroder et al., J. Biol Chem, May 17, 2000, Abstract (PMID:10816588).

Lerche et al. J. Biol Chem, Apr. 27, 2000, Abstract (PMID: 10787416).

S. William Tam et al., "Linopirdine A Depolarization–Activated Releaser of Transmitters for Treatment of Dimentia." Lilly Tang et al. eds., in *Neurochemistry in Clinical Application,* 1995, pp. 47–56.

* cited by examiner

*Primary Examiner*—Gary Kunz
*Assistant Examiner*—Sharon Turner
(74) *Attorney, Agent, or Firm*—Birch, Stewart, Kolasch & Birch, LLP

(57) ABSTRACT

This invention relates to novel potassium channels and genes encoding these channels. More specifically the invention provides isolated polynucleotides encoding the KCNQ5 potassium channel subunit, cells transformed with these polynucleotides, transgenic animals comprising genetic mutations, and the use of the transformed cells and the transgenic animals for the in vitro and in vivo screening of chemical compounds affecting KCNQ5 subunit containing potassium channels.

19 Claims, 11 Drawing Sheets

SEQUENCE LISTING

```
<160> NUMBER OF SEQ ID NOS: 10

<210> SEQ ID NO 1
<211> LENGTH: 3137
<212> TYPE: DNA
<213> ORGANISM: Homo sapiens
<220> FEATURE:
<221> NAME/KEY: CDS
<222> LOCATION: (1)..(2691)

<400> SEQUENCE: 1 atg aag gat gtg gag tcg ggc cgg ggc agg gtg ctg ctg aac tcg gca      48
Met Lys Asp Val Glu Ser Gly Arg Gly Arg Val Leu Leu Asn Ser Ala
 1               5                  10                  15 gcc gcc agg ggc gac ggc ctg cta ctg ctg ggc acc cgc gcg gcc acg      96
Ala Ala Arg Gly Asp Gly Leu Leu Leu Leu Gly Thr Arg Ala Ala Thr
             20                  25                  30 ctc ggt ggc ggc ggc ggt ggc ctg agg gag agc cgc cgg ggc aag cag     144
Leu Gly Gly Gly Gly Gly Gly Leu Arg Glu Ser Arg Arg Gly Lys Gln
         35                  40                  45 ggg gcc cgg atg agc ctg ctg ggg aag ccg ctc tct tac acg agt agc     192
Gly Ala Arg Met Ser Leu Leu Gly Lys Pro Leu Ser Tyr Thr Ser Ser
     50                  55                  60 cag agc tgc cgg cgc aac gtc aag tac cgg cgg gtg cag aac tac ctg     240
Gln Ser Cys Arg Arg Asn Val Lys Tyr Arg Arg Val Gln Asn Tyr Leu
 65                  70                  75                  80 tac aac gtg ctg gag aga ccc cgc ggc tgg gcg ttc atc tac cac gct     288
Tyr Asn Val Leu Glu Arg Pro Arg Gly Trp Ala Phe Ile Tyr His Ala
                 85                  90                  95 ttc gtt ttt ctc ctt gtc ttt ggt tgc ttg att ttg tca gtg ttt tct     336
Phe Val Phe Leu Leu Val Phe Gly Cys Leu Ile Leu Ser Val Phe Ser
            100                 105                 110 acc atc cct gag cac aca aaa ttg gcc tca agt tgc ctc ttg atc ctg     384
Thr Ile Pro Glu His Thr Lys Leu Ala Ser Ser Cys Leu Leu Ile Leu
        115                 120                 125 gag ttc gtg atg att gtc gtc ttt ggt ttg gag ttc atc att cga atc     432
Glu Phe Val Met Ile Val Val Phe Gly Leu Glu Phe Ile Ile Arg Ile
    130                 135                 140 tgg tct gcg ggt tgc tgt tgt cga tat aga gga tgg caa gga aga ctg     480
Trp Ser Ala Gly Cys Cys Cys Arg Tyr Arg Gly Trp Gln Gly Arg Leu
145                 150                 155                 160 agg ttt gct cga aag ccc ttc tgt gtt ata gat acc att gtt ctt atc     528
Arg Phe Ala Arg Lys Pro Phe Cys Val Ile Asp Thr Ile Val Leu Ile
                165                 170                 175
```

```
gct tca ata gca gtt gtt tct gca aaa act cag ggt aat att ttt gcc    576
Ala Ser Ile Ala Val Val Ser Ala Lys Thr Gln Gly Asn Ile Phe Ala
        180                 185                 190 acg tct gca ctc aga agt ctc cgt ttc cta cag atc ctc cgc atg gtg    624
Thr Ser Ala Leu Arg Ser Leu Arg Phe Leu Gln Ile Leu Arg Met Val
        195                 200                 205 cgc atg gac cga agg gga ggc act tgg aaa tta ctg ggt tca gtg gtt    672
Arg Met Asp Arg Arg Gly Gly Thr Trp Lys Leu Leu Gly Ser Val Val
    210                 215                 220 tat gct cac agc aag gaa tta atc aca gct tgg tac ata gga ttt ttg    720
Tyr Ala His Ser Lys Glu Leu Ile Thr Ala Trp Tyr Ile Gly Phe Leu
225                 230                 235                 240 gtt ctt att ttt tcg tct ttc ctt gtc tat ctg gtg gaa aag gat gcc    768
Val Leu Ile Phe Ser Ser Phe Leu Val Tyr Leu Val Glu Lys Asp Ala
                245                 250                 255 aat aaa gag ttt tct aca tat gca gat gct ctc tgg tgg gga aca att    816
Asn Lys Glu Phe Ser Thr Tyr Ala Asp Ala Leu Trp Trp Gly Thr Ile
            260                 265                 270 aca ttg aca act att ggc tat gga gac aaa act ccc cta act tgg ctg    864
Thr Leu Thr Thr Ile Gly Tyr Gly Asp Lys Thr Pro Leu Thr Trp Leu
        275                 280                 285 gga aga ttg ctt tct gca ggc ttt gca ctc ctt ggc att tct ttc ttt    912
Gly Arg Leu Leu Ser Ala Gly Phe Ala Leu Leu Gly Ile Ser Phe Phe
    290                 295                 300 gca ctt cct gcc ggc att ctt ggc tca ggt ttt gca tta aaa gta caa    960
Ala Leu Pro Ala Gly Ile Leu Gly Ser Gly Phe Ala Leu Lys Val Gln
305                 310                 315                 320 gaa caa cac cgc cag aaa cac ttt gag aaa aga agg aac cca gct gcc    1008
Glu Gln His Arg Gln Lys His Phe Glu Lys Arg Arg Asn Pro Ala Ala
                325                 330                 335 aac ctc att cag tgt gtt tgg cgt agt tac gca gct gat gag aaa tct    1056
Asn Leu Ile Gln Cys Val Trp Arg Ser Tyr Ala Ala Asp Glu Lys Ser
            340                 345                 350 gtt tcc att gca acc tgg aag cca cac ttg aag gcc ttg cac acc tgc    1104
Val Ser Ile Ala Thr Trp Lys Pro His Leu Lys Ala Leu His Thr Cys
        355                 360                 365 agc cct acc aag aaa gaa caa ggg gaa gca tca agc agt cag aag cta    1152
Ser Pro Thr Lys Lys Glu Gln Gly Glu Ala Ser Ser Ser Gln Lys Leu
    370                 375                 380 agt ttt aag gag cga gtg cgc atg gct agc ccc agg ggc cag agt att    1200
Ser Phe Lys Glu Arg Val Arg Met Ala Ser Pro Arg Gly Gln Ser Ile
385                 390                 395                 400 aag agc cga caa gcc tca gta ggt gac agg agg tcc cca agc acc gac    1248
Lys Ser Arg Gln Ala Ser Val Gly Asp Arg Arg Ser Pro Ser Thr Asp
                405                 410                 415 atc aca gcc gag ggc agt ccc acc aaa gtg cag aag agc tgg agc ttc    1296
Ile Thr Ala Glu Gly Ser Pro Thr Lys Val Gln Lys Ser Trp Ser Phe
            420                 425                 430 aac gac cga acc cgc ttc cgg ccc tcg ctg cgc ctc aaa agt tct cag    1344
Asn Asp Arg Thr Arg Phe Arg Pro Ser Leu Arg Leu Lys Ser Ser Gln
        435                 440                 445 cca aaa cca gtg ata gat gct gac aca gcc ctt ggc act gat gat gta    1392
Pro Lys Pro Val Ile Asp Ala Asp Thr Ala Leu Gly Thr Asp Asp Val
    450                 455                 460 tat gat gaa aaa gga tgc cag tgt gat gta tca gtg gaa gac ctc acc    1440
Tyr Asp Glu Lys Gly Cys Gln Cys Asp Val Ser Val Glu Asp Leu Thr
465                 470                 475                 480 cca cca ctt aaa act gtc att cga gct atc aga att atg aaa ttt cat    1488
Pro Pro Leu Lys Thr Val Ile Arg Ala Ile Arg Ile Met Lys Phe His
```

-continued

|  |  |  | 485 |  |  |  | 490 |  |  |  | 495 |  |  |  |  |
|---|---|---|---|---|---|---|---|---|---|---|---|---|---|---|---|
| gtt | gca | aaa | cgg | aag | ttt | aag | gaa | aca | tta | cgt | cca | tat | gat | gta | aaa | 1536 |
| Val | Ala | Lys | Arg | Lys | Phe | Lys | Glu | Thr | Leu | Arg | Pro | Tyr | Asp | Val | Lys |
|  |  |  | 500 |  |  |  | 505 |  |  |  | 510 |  |  |  |  |

| gat | gtc | att | gaa | caa | tat | tct | gct | ggt | cat | ctg | gac | atg | ttg | tgt | aga | 1584 |
| Asp | Val | Ile | Glu | Gln | Tyr | Ser | Ala | Gly | His | Leu | Asp | Met | Leu | Cys | Arg |
|  |  | 515 |  |  |  |  | 520 |  |  |  |  | 525 |  |  |  |

| att | aaa | agc | ctt | caa | aca | cgt | gtt | gat | caa | att | ctt | gga | aaa | ggg | caa | 1632 |
| Ile | Lys | Ser | Leu | Gln | Thr | Arg | Val | Asp | Gln | Ile | Leu | Gly | Lys | Gly | Gln |
|  | 530 |  |  |  |  | 535 |  |  |  |  | 540 |  |  |  |  |

| atc | aca | tca | gat | aag | aag | agc | cga | gag | aaa | ata | aca | gca | gaa | cat | gag | 1680 |
| Ile | Thr | Ser | Asp | Lys | Lys | Ser | Arg | Glu | Lys | Ile | Thr | Ala | Glu | His | Glu |
| 545 |  |  |  |  | 550 |  |  |  |  | 555 |  |  |  |  | 560 |

| acc | aca | gac | gat | ctc | agt | atg | ctc | ggt | cgg | gtg | gtc | aag | gtt | gaa | aaa | 1728 |
| Thr | Thr | Asp | Asp | Leu | Ser | Met | Leu | Gly | Arg | Val | Val | Lys | Val | Glu | Lys |
|  |  |  |  | 565 |  |  |  |  | 570 |  |  |  |  | 575 |  |

| cag | gta | cag | tcc | ata | gaa | tcc | aag | ctg | gac | tgc | cta | cta | gac | atc | tat | 1776 |
| Gln | Val | Gln | Ser | Ile | Glu | Ser | Lys | Leu | Asp | Cys | Leu | Leu | Asp | Ile | Tyr |
|  |  |  | 580 |  |  |  |  | 585 |  |  |  |  | 590 |  |  |

| caa | cag | gtc | ctt | cgg | aaa | ggc | tct | gcc | tca | gcc | ctc | gct | ttg | gct | tca | 1824 |
| Gln | Gln | Val | Leu | Arg | Lys | Gly | Ser | Ala | Ser | Ala | Leu | Ala | Leu | Ala | Ser |
|  |  | 595 |  |  |  |  | 600 |  |  |  |  | 605 |  |  |  |

| ttc | cag | atc | cca | cct | ttt | gaa | tgt | gaa | cag | aca | tct | gac | tat | caa | agc | 1872 |
| Phe | Gln | Ile | Pro | Pro | Phe | Glu | Cys | Glu | Gln | Thr | Ser | Asp | Tyr | Gln | Ser |
|  |  | 610 |  |  |  |  | 615 |  |  |  |  | 620 |  |  |  |

| cct | gtg | gat | agc | aaa | gat | ctt | tcg | ggt | tcc | gca | caa | aac | agt | ggc | tgc | 1920 |
| Pro | Val | Asp | Ser | Lys | Asp | Leu | Ser | Gly | Ser | Ala | Gln | Asn | Ser | Gly | Cys |
| 625 |  |  |  |  | 630 |  |  |  |  | 635 |  |  |  |  | 640 |

| tta | tcc | aga | tca | act | agt | gcc | aac | atc | tcg | aga | ggc | ctg | cag | ttc | att | 1968 |
| Leu | Ser | Arg | Ser | Thr | Ser | Ala | Asn | Ile | Ser | Arg | Gly | Leu | Gln | Phe | Ile |
|  |  |  |  | 645 |  |  |  |  | 650 |  |  |  |  | 655 |  |

| ctg | acg | cca | aat | gag | ttc | agt | gcc | cag | act | ttc | tac | gcg | ctt | agc | cct | 2016 |
| Leu | Thr | Pro | Asn | Glu | Phe | Ser | Ala | Gln | Thr | Phe | Tyr | Ala | Leu | Ser | Pro |
|  |  |  | 660 |  |  |  |  | 665 |  |  |  |  | 670 |  |  |

| act | atg | cac | agt | caa | gca | aca | cag | gtg | cca | att | agt | caa | agc | gat | ggc | 2064 |
| Thr | Met | His | Ser | Gln | Ala | Thr | Gln | Val | Pro | Ile | Ser | Gln | Ser | Asp | Gly |
|  |  | 675 |  |  |  |  | 680 |  |  |  |  | 685 |  |  |  |

| tca | gca | gtg | gca | gcc | acc | aac | acc | att | gca | aac | caa | ata | aat | acg | gca | 2112 |
| Ser | Ala | Val | Ala | Ala | Thr | Asn | Thr | Ile | Ala | Asn | Gln | Ile | Asn | Thr | Ala |
|  | 690 |  |  |  |  | 695 |  |  |  |  | 700 |  |  |  |  |

| ccc | aag | cca | gca | gcc | cca | aca | act | tta | cag | atc | cca | cct | ctc | cca | 2160 |
| Pro | Lys | Pro | Ala | Ala | Pro | Thr | Thr | Leu | Gln | Ile | Pro | Pro | Leu | Pro |
| 705 |  |  |  | 710 |  |  |  |  | 715 |  |  |  |  | 720 |

| gcc | atc | aag | cat | ctg | ccc | agg | cca | gaa | act | ctg | cac | cct | aac | cct | gca | 2208 |
| Ala | Ile | Lys | His | Leu | Pro | Arg | Pro | Glu | Thr | Leu | His | Pro | Asn | Pro | Ala |
|  |  |  |  | 725 |  |  |  |  | 730 |  |  |  |  | 735 |  |

| ggc | tta | cag | gaa | agc | att | tct | gac | gtc | acc | acc | tgc | ctt | gtt | gcc | tcc | 2256 |
| Gly | Leu | Gln | Glu | Ser | Ile | Ser | Asp | Val | Thr | Thr | Cys | Leu | Val | Ala | Ser |
|  |  |  | 740 |  |  |  |  | 745 |  |  |  |  | 750 |  |  |

| aag | gaa | aat | gtt | cag | gtt | gca | cag | tca | aat | ctc | acc | aag | gac | cgt | tct | 2304 |
| Lys | Glu | Asn | Val | Gln | Val | Ala | Gln | Ser | Asn | Leu | Thr | Lys | Asp | Arg | Ser |
|  |  | 755 |  |  |  |  | 760 |  |  |  |  | 765 |  |  |  |

| atg | agg | aaa | agc | ttt | gac | atg | gga | gga | gaa | act | ctg | ttg | tct | gtc | tgt | 2352 |
| Met | Arg | Lys | Ser | Phe | Asp | Met | Gly | Gly | Glu | Thr | Leu | Leu | Ser | Val | Cys |
|  | 770 |  |  |  |  | 775 |  |  |  |  | 780 |  |  |  |  |

| ccc | atg | gtg | ccg | aag | gac | ttg | ggc | aaa | tct | ttg | tct | gtg | caa | aac | ctg | 2400 |
| Pro | Met | Val | Pro | Lys | Asp | Leu | Gly | Lys | Ser | Leu | Ser | Val | Gln | Asn | Leu |
| 785 |  |  |  |  | 790 |  |  |  |  | 795 |  |  |  |  | 800 |

| atc | agg | tcg | acc | gag | gaa | ctg | aat | ata | caa | ctt | tca | ggg | agt | gag | tca | 2448 |

-continued

| | | | | | | | | | | | | |
|---|---|---|---|---|---|---|---|---|---|---|---|---|
| Ile | Arg | Ser | Thr | Glu 805 | Glu | Leu | Asn | Ile 810 | Gln | Leu | Ser | Gly | Ser | Glu 815 | Ser |

```
agt ggc tcc aga ggc agc caa gat ttt tac ccc aaa tgg agg gaa tcc    2496
Ser Gly Ser Arg Gly Ser Gln Asp Phe Tyr Pro Lys Trp Arg Glu Ser
        820                 825                 830 aaa ttg ttt ata act gat gaa gag gtg ggt ccc gaa gag aca gag aca    2544
Lys Leu Phe Ile Thr Asp Glu Glu Val Gly Pro Glu Glu Thr Glu Thr
            835                 840                 845 gac act ttt gat gcc gca ccg cag cct gcc agg gaa gct gcc ttt gca    2592
Asp Thr Phe Asp Ala Ala Pro Gln Pro Ala Arg Glu Ala Ala Phe Ala
    850                 855                 860 tca gac tct cta agg act gga agg tca cga tca tct cag agc att tgt    2640
Ser Asp Ser Leu Arg Thr Gly Arg Ser Arg Ser Ser Gln Ser Ile Cys
865                 870                 875                 880 aag gca gga gaa agt aca gat gcc ctc agc ttg cct cat gtc aaa ctg    2688
Lys Ala Gly Glu Ser Thr Asp Ala Leu Ser Leu Pro His Val Lys Leu
                885                 890                 895 aaa taagttcttc attttctttc caggcatagc agttctttag ccatacatat          2741
Lys cattgcatga actatttcga aagcccttct aaaaagttga aattgcaaga atcgggaaga   2801
acatgaaagg cagtttataa gcccgttacc ttttaattgc atgaaaatgc atgtttaggg   2861
atggctaaaa ttccaaggtg catcgacatt aacccactca tttagtaatg taccttgagt   2921
taaaaagcct gagaaaccaa acacagctaa tgctatgggg tgtatgaata tgtcaagttt   2981
aggtcattta gaagatttga cactgtattt tgaaattatg ggagtaaaca ccttcaaatt   3041
tcaggcattt ctgctttgtg actaaataca aactacattt tcaagattag gccataatgt   3101
atatttaaac acaatggcta tcaacagctg ctaata                            3137
```

<210> SEQ ID NO 2
<211> LENGTH: 897
<212> TYPE: PRT
<213> ORGANISM: Homo sapiens

<400> SEQUENCE: 2

Met Lys Asp Val Glu Ser Gly Arg Gly Arg Val Leu Leu Asn Ser Ala
 1               5                  10                  15

Ala Ala Arg Gly Asp Gly Leu Leu Leu Gly Thr Arg Ala Ala Thr
            20                  25                  30

Leu Gly Gly Gly Gly Gly Leu Arg Glu Ser Arg Arg Gly Lys Gln
        35                  40                  45

Gly Ala Arg Met Ser Leu Leu Gly Lys Pro Leu Ser Tyr Thr Ser Ser
    50                  55                  60

Gln Ser Cys Arg Arg Asn Val Lys Tyr Arg Arg Val Gln Asn Tyr Leu
65                  70                  75                  80

Tyr Asn Val Leu Glu Arg Pro Arg Gly Trp Ala Phe Ile Tyr His Ala
                85                  90                  95

Phe Val Phe Leu Leu Val Phe Gly Cys Leu Ile Leu Ser Val Phe Ser
            100                 105                 110

Thr Ile Pro Glu His Thr Lys Leu Ala Ser Ser Cys Leu Leu Ile Leu
        115                 120                 125

Glu Phe Val Met Ile Val Val Phe Gly Leu Glu Phe Ile Ile Arg Ile
    130                 135                 140

Trp Ser Ala Gly Cys Cys Cys Arg Tyr Arg Gly Trp Gln Gly Arg Leu
145                 150                 155                 160

Arg Phe Ala Arg Lys Pro Phe Cys Val Ile Asp Thr Ile Val Leu Ile

-continued

```
                165                 170                 175
Ala Ser Ile Ala Val Val Ser Ala Lys Thr Gln Gly Asn Ile Phe Ala
            180                 185                 190
Thr Ser Ala Leu Arg Ser Leu Arg Phe Leu Gln Ile Leu Arg Met Val
            195                 200                 205
Arg Met Asp Arg Arg Gly Gly Thr Trp Lys Leu Leu Gly Ser Val Val
    210                 215                 220
Tyr Ala His Ser Lys Glu Leu Ile Thr Ala Trp Tyr Ile Gly Phe Leu
225                 230                 235                 240
Val Leu Ile Phe Ser Ser Phe Leu Val Tyr Leu Val Glu Lys Asp Ala
                245                 250                 255
Asn Lys Glu Phe Ser Thr Tyr Ala Asp Ala Leu Trp Trp Gly Thr Ile
            260                 265                 270
Thr Leu Thr Thr Ile Gly Tyr Gly Asp Lys Thr Pro Leu Thr Trp Leu
            275                 280                 285
Gly Arg Leu Leu Ser Ala Gly Phe Ala Leu Leu Gly Ile Ser Phe Phe
    290                 295                 300
Ala Leu Pro Ala Gly Ile Leu Gly Ser Gly Phe Ala Leu Lys Val Gln
305                 310                 315                 320
Glu Gln His Arg Gln Lys His Phe Glu Lys Arg Arg Asn Pro Ala Ala
                325                 330                 335
Asn Leu Ile Gln Cys Val Trp Arg Ser Tyr Ala Ala Asp Glu Lys Ser
            340                 345                 350
Val Ser Ile Ala Thr Trp Lys Pro His Leu Lys Ala Leu His Thr Cys
            355                 360                 365
Ser Pro Thr Lys Lys Glu Gln Gly Glu Ala Ser Ser Ser Gln Lys Leu
    370                 375                 380
Ser Phe Lys Glu Arg Val Arg Met Ala Ser Pro Arg Gly Gln Ser Ile
385                 390                 395                 400
Lys Ser Arg Gln Ala Ser Val Gly Asp Arg Arg Ser Pro Ser Thr Asp
                405                 410                 415
Ile Thr Ala Glu Gly Ser Pro Thr Lys Val Gln Lys Ser Trp Ser Phe
            420                 425                 430
Asn Asp Arg Thr Arg Phe Arg Pro Ser Leu Arg Leu Lys Ser Ser Gln
            435                 440                 445
Pro Lys Pro Val Ile Asp Ala Asp Thr Ala Leu Gly Thr Asp Asp Val
    450                 455                 460
Tyr Asp Glu Lys Gly Cys Gln Cys Asp Val Ser Val Glu Asp Leu Thr
465                 470                 475                 480
Pro Pro Leu Lys Thr Val Ile Arg Ala Ile Arg Ile Met Lys Phe His
                485                 490                 495
Val Ala Lys Arg Lys Phe Lys Glu Thr Leu Arg Pro Tyr Asp Val Lys
            500                 505                 510
Asp Val Ile Glu Gln Tyr Ser Ala Gly His Leu Asp Met Leu Cys Arg
            515                 520                 525
Ile Lys Ser Leu Gln Thr Arg Val Asp Gln Ile Leu Gly Lys Gly Gln
    530                 535                 540
Ile Thr Ser Asp Lys Lys Ser Arg Glu Lys Ile Thr Ala Glu His Glu
545                 550                 555                 560
Thr Thr Asp Asp Leu Ser Met Leu Gly Arg Val Val Lys Val Glu Lys
                565                 570                 575
Gln Val Gln Ser Ile Glu Ser Lys Leu Asp Cys Leu Leu Asp Ile Tyr
            580                 585                 590
```

```
Gln Gln Val Leu Arg Lys Gly Ser Ala Ser Ala Leu Ala Leu Ala Ser
            595                 600                 605

Phe Gln Ile Pro Pro Phe Glu Cys Glu Gln Thr Ser Asp Tyr Gln Ser
            610                 615                 620

Pro Val Asp Ser Lys Asp Leu Ser Gly Ser Ala Gln Asn Ser Gly Cys
625                 630                 635                 640

Leu Ser Arg Ser Thr Ser Ala Asn Ile Ser Arg Gly Leu Gln Phe Ile
            645                 650                 655

Leu Thr Pro Asn Glu Phe Ser Ala Gln Thr Phe Tyr Ala Leu Ser Pro
            660                 665                 670

Thr Met His Ser Gln Ala Thr Gln Val Pro Ile Ser Gln Ser Asp Gly
            675                 680                 685

Ser Ala Val Ala Ala Thr Asn Thr Ile Ala Asn Gln Ile Asn Thr Ala
690                 695                 700

Pro Lys Pro Ala Ala Pro Thr Thr Leu Gln Ile Pro Pro Leu Pro
705                 710                 715                 720

Ala Ile Lys His Leu Pro Arg Pro Glu Thr Leu His Pro Asn Pro Ala
            725                 730                 735

Gly Leu Gln Glu Ser Ile Ser Asp Val Thr Thr Cys Leu Val Ala Ser
            740                 745                 750

Lys Glu Asn Val Gln Val Ala Gln Ser Asn Leu Thr Lys Asp Arg Ser
            755                 760                 765

Met Arg Lys Ser Phe Asp Met Gly Gly Glu Thr Leu Leu Ser Val Cys
            770                 775                 780

Pro Met Val Pro Lys Asp Leu Gly Lys Ser Leu Ser Val Gln Asn Leu
785                 790                 795                 800

Ile Arg Ser Thr Glu Glu Leu Asn Ile Gln Leu Ser Gly Ser Glu Ser
            805                 810                 815

Ser Gly Ser Arg Gly Ser Gln Asp Phe Tyr Pro Lys Trp Arg Glu Ser
            820                 825                 830

Lys Leu Phe Ile Thr Asp Glu Glu Val Gly Pro Glu Glu Thr Glu Thr
            835                 840                 845

Asp Thr Phe Asp Ala Ala Pro Gln Pro Ala Arg Glu Ala Ala Phe Ala
850                 855                 860

Ser Asp Ser Leu Arg Thr Gly Arg Ser Arg Ser Gln Ser Ile Cys
865                 870                 875                 880

Lys Ala Gly Glu Ser Thr Asp Ala Leu Ser Leu Pro His Val Lys Leu
            885                 890                 895

Lys

<210> SEQ ID NO 3
<211> LENGTH: 676
<212> TYPE: PRT
<213> ORGANISM: Homo sapiens

<400> SEQUENCE: 3

Met Ala Ala Ala Ser Ser Pro Arg Ala Glu Arg Lys Arg Trp Gly
1               5                   10                  15

Trp Gly Arg Leu Pro Gly Ala Arg Arg Gly Ser Ala Gly Leu Ala Lys
            20                  25                  30

Lys Cys Pro Phe Ser Leu Glu Leu Ala Glu Gly Gly Pro Ala Gly Gly
            35                  40                  45

Ala Leu Tyr Ala Pro Ile Ala Pro Gly Ala Pro Gly Pro Ala Pro Pro
50                  55                  60
```

-continued

```
Ala Ser Pro Ala Ala Pro Ala Pro Pro Val Ala Ser Asp Leu Gly
 65                  70                  75                  80

Pro Arg Pro Pro Val Ser Leu Asp Pro Arg Val Ser Ile Tyr Ser Thr
                 85                  90                  95

Arg Arg Pro Val Leu Ala Arg Thr His Val Gln Gly Arg Val Tyr Asn
            100                 105                 110

Phe Leu Glu Arg Pro Thr Gly Trp Lys Cys Phe Val Tyr His Phe Ala
        115                 120                 125

Val Phe Leu Ile Val Leu Val Cys Leu Ile Phe Ser Val Leu Ser Thr
    130                 135                 140

Ile Glu Gln Tyr Ala Ala Leu Ala Thr Gly Thr Leu Phe Trp Met Glu
145                 150                 155                 160

Ile Val Leu Val Val Phe Phe Gly Thr Glu Tyr Val Val Arg Leu Trp
                165                 170                 175

Ser Ala Gly Cys Arg Ser Lys Tyr Val Gly Leu Trp Gly Arg Leu Arg
            180                 185                 190

Phe Ala Arg Lys Pro Ile Ser Ile Ile Asp Leu Ile Val Val Val Ala
        195                 200                 205

Ser Met Val Val Leu Cys Val Gly Ser Lys Gly Gln Val Phe Ala Thr
    210                 215                 220

Ser Ala Ile Arg Gly Ile Arg Phe Leu Gln Ile Leu Arg Met Leu His
225                 230                 235                 240

Val Asp Arg Gln Gly Gly Thr Trp Arg Leu Leu Gly Ser Val Val Phe
                245                 250                 255

Ile His Arg Gln Glu Leu Ile Thr Thr Leu Tyr Ile Gly Phe Leu Gly
            260                 265                 270

Leu Ile Phe Ser Ser Tyr Phe Val Tyr Leu Ala Glu Lys Asp Ala Val
        275                 280                 285

Asn Glu Ser Gly Arg Val Glu Phe Gly Ser Tyr Ala Asp Ala Leu Trp
    290                 295                 300

Trp Gly Val Val Thr Val Thr Thr Ile Gly Tyr Gly Asp Lys Val Pro
305                 310                 315                 320

Gln Thr Trp Val Gly Lys Thr Ile Ala Ser Cys Phe Ser Val Phe Ala
                325                 330                 335

Ile Ser Phe Phe Ala Leu Pro Ala Gly Ile Leu Gly Ser Gly Phe Ala
            340                 345                 350

Leu Lys Val Gln Gln Lys Gln Arg Gln Lys His Phe Asn Arg Gln Ile
        355                 360                 365

Pro Ala Ala Ala Ser Leu Ile Gln Thr Ala Trp Arg Cys Tyr Ala Ala
    370                 375                 380

Glu Asn Pro Asp Ser Ser Thr Trp Lys Ile Tyr Ile Arg Lys Ala Pro
385                 390                 395                 400

Arg Ser His Thr Leu Leu Ser Pro Ser Pro Lys Pro Lys Lys Ser Val
                405                 410                 415

Val Val Lys Lys Lys Lys Phe Lys Leu Asp Lys Asp Asn Gly Val Thr
            420                 425                 430

Pro Gly Glu Lys Met Leu Thr Val Pro His Ile Thr Cys Asp Pro Pro
        435                 440                 445

Glu Glu Arg Arg Leu Asp His Phe Ser Val Asp Gly Tyr Asp Ser Ser
    450                 455                 460

Val Arg Lys Ser Pro Thr Leu Leu Glu Val Ser Met Pro His Phe Met
465                 470                 475                 480
```

-continued

```
Arg Thr Asn Ser Phe Ala Glu Asp Leu Asp Leu Glu Gly Glu Thr Leu
            485                 490                 495

Leu Thr Pro Ile Thr His Ile Ser Gln Leu Arg Glu His His Arg Ala
            500                 505                 510

Thr Ile Lys Val Ile Arg Arg Met Gln Tyr Phe Val Ala Lys Lys Lys
            515                 520                 525

Phe Gln Gln Ala Arg Lys Pro Tyr Asp Val Arg Asp Val Ile Glu Gln
        530                 535                 540

Tyr Ser Gln Gly His Leu Asn Leu Met Val Arg Ile Lys Glu Leu Gln
545                 550                 555                 560

Arg Arg Leu Asp Gln Ser Ile Gly Lys Pro Ser Leu Phe Ile Ser Val
            565                 570                 575

Ser Glu Lys Ser Lys Asp Arg Gly Ser Asn Thr Ile Gly Ala Arg Leu
            580                 585                 590

Asn Arg Val Glu Asp Lys Val Thr Gln Leu Asp Gln Arg Leu Ala Leu
            595                 600                 605

Ile Thr Asp Met Leu His Gln Leu Leu Ser Leu His Gly Gly Ser Thr
        610                 615                 620

Pro Gly Ser Gly Gly Pro Arg Glu Gly Gly Ala His Ile Thr Gln
625                 630                 635                 640

Pro Cys Gly Ser Gly Ser Val Asp Pro Glu Leu Phe Leu Pro Ser
            645                 650                 655

Asn Thr Leu Pro Thr Tyr Glu Gln Leu Thr Val Pro Arg Arg Gly Pro
            660                 665                 670

Asp Glu Gly Ser
        675

<210> SEQ ID NO 4
<211> LENGTH: 844
<212> TYPE: PRT
<213> ORGANISM: Homo sapiens

<400> SEQUENCE: 4

Met Val Gln Lys Ser Arg Asn Gly Gly Val Tyr Pro Gly Pro Ser Gly
1               5                  10                  15

Glu Lys Lys Leu Lys Val Gly Phe Val Gly Leu Asp Pro Gly Ala Pro
            20                  25                  30

Asp Ser Thr Arg Asp Gly Ala Leu Leu Ile Ala Gly Ser Glu Ala Pro
            35                  40                  45

Lys Arg Gly Ser Ile Leu Ser Lys Pro Arg Ala Gly Ala Gly Ala
        50                  55                  60

Gly Lys Pro Pro Lys Arg Asn Ala Phe Tyr Arg Lys Leu Gln Asn Phe
65                  70                  75                  80

Leu Tyr Asn Val Leu Glu Arg Pro Arg Gly Trp Ala Phe Ile Tyr His
                85                  90                  95

Ala Tyr Val Phe Leu Leu Val Phe Ser Cys Leu Val Leu Ser Val Phe
            100                 105                 110

Ser Thr Ile Lys Glu Tyr Glu Lys Ser Ser Glu Gly Ala Leu Tyr Ile
            115                 120                 125

Leu Glu Ile Val Thr Ile Val Val Phe Gly Val Glu Tyr Phe Val Arg
        130                 135                 140

Ile Trp Ala Ala Gly Cys Cys Cys Arg Tyr Arg Gly Trp Arg Gly Arg
145                 150                 155                 160

Leu Lys Phe Ala Arg Lys Pro Phe Cys Val Ile Asp Ile Met Val Leu
                165                 170                 175
```

-continued

```
Ile Ala Ser Ile Ala Val Leu Ala Gly Ser Gln Gly Asn Val Phe
            180                 185                 190
Ala Thr Ser Ala Leu Arg Ser Leu Arg Phe Leu Gln Ile Leu Arg Met
        195                 200                 205
Ile Arg Met Asp Arg Arg Gly Gly Thr Trp Lys Leu Leu Gly Ser Val
    210                 215                 220
Val Tyr Ala His Ser Lys Glu Leu Val Thr Ala Trp Tyr Ile Gly Phe
225                 230                 235                 240
Leu Cys Leu Ile Leu Ala Ser Phe Leu Val Tyr Leu Ala Glu Lys Gly
                245                 250                 255
Glu Asn Asp His Phe Asp Thr Tyr Ala Asp Ala Leu Trp Trp Gly Leu
            260                 265                 270
Ile Thr Leu Thr Thr Ile Gly Tyr Gly Asp Lys Tyr Pro Gln Thr Trp
        275                 280                 285
Asn Gly Arg Leu Leu Ala Ala Thr Phe Thr Leu Ile Gly Val Ser Phe
    290                 295                 300
Phe Ala Leu Pro Ala Gly Ile Leu Gly Ser Gly Phe Ala Leu Lys Val
305                 310                 315                 320
Gln Glu Gln His Arg Gln Lys His Phe Glu Lys Arg Arg Asn Pro Ala
                325                 330                 335
Ala Gly Leu Ile Gln Ser Ala Trp Arg Phe Tyr Ala Thr Asn Leu Ser
            340                 345                 350
Arg Thr Asp Leu His Ser Thr Trp Gln Tyr Tyr Glu Arg Thr Val Thr
        355                 360                 365
Val Pro Met Tyr Arg Leu Ile Pro Pro Leu Asn Gln Leu Glu Leu Leu
    370                 375                 380
Arg Asn Leu Lys Ser Lys Ser Gly Leu Ala Phe Arg Lys Asp Pro Pro
385                 390                 395                 400
Pro Glu Pro Ser Pro Ser Gln Lys Val Ser Leu Lys Asp Arg Val Phe
                405                 410                 415
Ser Ser Pro Arg Gly Val Ala Ala Lys Gly Lys Gly Ser Pro Gln Ala
            420                 425                 430
Gln Thr Val Arg Arg Ser Pro Ser Ala Asp Gln Ser Leu Glu Asp Ser
        435                 440                 445
Pro Ser Lys Val Pro Lys Ser Trp Ser Phe Gly Asp Arg Ser Arg Ala
    450                 455                 460
Arg Gln Ala Phe Arg Ile Lys Gly Ala Ala Ser Arg Gln Asn Ser Glu
465                 470                 475                 480
Glu Ala Ser Leu Pro Gly Glu Asp Ile Val Asp Asp Lys Ser Cys Pro
                485                 490                 495
Cys Glu Phe Val Thr Glu Asp Leu Thr Pro Gly Leu Lys Val Ser Ile
            500                 505                 510
Arg Ala Val Cys Val Met Arg Phe Leu Val Ser Lys Arg Lys Phe Lys
        515                 520                 525
Glu Ser Leu Arg Pro Tyr Asp Val Met Asp Val Ile Glu Gln Tyr Ser
    530                 535                 540
Ala Gly His Leu Asp Met Leu Ser Arg Ile Lys Ser Leu Gln Ser Arg
545                 550                 555                 560
Val Asp Gln Ile Val Gly Arg Gly Pro Ala Ile Thr Asp Lys Asp Arg
                565                 570                 575
Thr Lys Gly Pro Ala Glu Ala Glu Leu Pro Glu Asp Pro Ser Met Met
            580                 585                 590
```

-continued

```
Gly Arg Leu Gly Lys Val Glu Lys Gln Val Leu Ser Met Glu Lys Lys
            595                 600                 605

Leu Asp Phe Leu Val Asn Ile Tyr Met Gln Arg Met Gly Ile Pro Pro
            610                 615                 620

Thr Glu Thr Glu Ala Tyr Phe Gly Ala Lys Glu Pro Glu Pro Ala Pro
625                 630                 635                 640

Pro Tyr His Ser Pro Glu Asp Ser Arg Glu His Val Asp Arg His Gly
                645                 650                 655

Cys Ile Val Lys Ile Val Arg Ser Ser Ser Thr Gly Gln Lys Asn
            660                 665                 670

Phe Ser Ala Pro Pro Ala Ala Pro Val Gln Cys Pro Pro Ser Thr
            675                 680                 685

Ser Trp Gln Pro Gln Ser His Pro Arg Gln Gly His Gly Thr Ser Pro
            690                 695                 700

Val Gly Asp His Gly Ser Leu Val Arg Ile Pro Pro Pro Ala His
705                 710                 715                 720

Glu Arg Ser Leu Ser Ala Tyr Gly Gly Asn Arg Ala Ser Met Glu
                725                 730                 735

Phe Leu Arg Gln Glu Asp Thr Pro Gly Cys Arg Pro Glu Gly Thr
            740                 745                 750

Leu Arg Asp Ser Asp Thr Ser Ile Ser Ile Pro Ser Val Asp His Glu
            755                 760                 765

Glu Leu Glu Arg Ser Phe Ser Gly Phe Ser Ile Ser Gln Ser Lys Glu
            770                 775                 780

Asn Leu Asp Ala Leu Asn Ser Cys Tyr Ala Ala Val Ala Pro Cys Ala
785                 790                 795                 800

Lys Val Arg Pro Tyr Ile Ala Glu Gly Glu Ser Asp Thr Asp Ser Asp
                805                 810                 815

Leu Cys Thr Pro Cys Gly Pro Pro Arg Ser Ala Thr Gly Glu Gly
            820                 825                 830

Pro Phe Gly Asp Val Gly Trp Ala Gly Pro Arg Lys
            835                 840
```

<210> SEQ ID NO 5
<211> LENGTH: 872
<212> TYPE: PRT
<213> ORGANISM: Homo sapiens

<400> SEQUENCE: 5

```
Met Gly Leu Lys Ala Arg Arg Ala Ala Gly Ala Ala Gly Gly Gly Gly
1               5                   10                  15

Asp Gly Gly Gly Gly Gly Gly Ala Ala Asn Pro Ala Gly Gly Asp
            20                  25                  30

Ala Ala Ala Ala Gly Asp Glu Glu Arg Lys Val Gly Leu Ala Pro Gly
            35                  40                  45

Asp Val Glu Gln Val Thr Leu Ala Leu Gly Ala Gly Ala Asp Lys Asp
50                  55                  60

Gly Thr Leu Leu Leu Glu Gly Gly Arg Asp Glu Gly Gln Arg Arg
65                  70                  75                  80

Thr Pro Gln Gly Ile Gly Leu Leu Ala Lys Thr Pro Leu Ser Arg Pro
                85                  90                  95

Val Lys Arg Asn Asn Ala Lys Tyr Arg Arg Ile Gln Thr Leu Ile Tyr
            100                 105                 110

Asp Ala Leu Glu Arg Pro Arg Gly Trp Ala Leu Leu Tyr His Ala Leu
            115                 120                 125
```

```
Val Phe Leu Ile Val Leu Gly Cys Leu Ile Leu Ala Val Leu Thr Thr
    130                 135                 140

Phe Lys Glu Tyr Glu Thr Val Ser Gly Asp Trp Leu Leu Leu Glu
145                 150                 155                 160

Thr Phe Ala Ile Phe Ile Phe Gly Ala Glu Phe Ala Leu Arg Ile Trp
                165                 170                 175

Ala Ala Gly Cys Cys Arg Tyr Lys Gly Trp Arg Gly Arg Leu Lys
                180                 185                 190

Phe Ala Arg Lys Pro Leu Cys Met Leu Asp Ile Phe Val Leu Ile Ala
                195                 200                 205

Ser Val Pro Val Val Ala Val Gly Asn Gln Gly Asn Val Leu Ala Thr
    210                 215                 220

Ser Leu Arg Ser Leu Arg Phe Leu Gln Ile Leu Arg Met Leu Arg Met
225                 230                 235                 240

Asp Arg Arg Gly Gly Thr Trp Lys Leu Leu Gly Ser Ala Ile Cys Ala
                245                 250                 255

His Ser Lys Glu Leu Ile Thr Ala Trp Tyr Ile Gly Phe Leu Thr Leu
                260                 265                 270

Ile Leu Ser Ser Phe Leu Val Tyr Leu Val Glu Lys Asp Val Pro Glu
    275                 280                 285

Val Asp Ala Gln Gly Glu Glu Met Lys Glu Glu Phe Glu Thr Tyr Ala
    290                 295                 300

Asp Ala Leu Trp Trp Gly Leu Ile Thr Leu Ala Thr Ile Gly Tyr Gly
305                 310                 315                 320

Asp Lys Thr Pro Lys Thr Trp Glu Gly Arg Leu Ile Ala Ala Thr Phe
                325                 330                 335

Ser Leu Ile Gly Val Ser Phe Phe Ala Leu Pro Ala Gly Ile Leu Gly
                340                 345                 350

Ser Gly Leu Ala Leu Lys Val Gln Glu Gln His Arg Gln Lys His Phe
                355                 360                 365

Glu Lys Arg Arg Lys Pro Ala Ala Glu Leu Ile Gln Ala Ala Trp Arg
    370                 375                 380

Tyr Tyr Ala Thr Asn Pro Asn Arg Ile Asp Leu Val Ala Thr Trp Arg
385                 390                 395                 400

Phe Tyr Glu Ser Val Val Ser Phe Pro Phe Phe Arg Lys Glu Gln Leu
                405                 410                 415

Glu Ala Ala Ser Ser Gln Lys Leu Gly Leu Leu Asp Arg Val Arg Leu
                420                 425                 430

Ser Asn Pro Arg Gly Ser Asn Thr Lys Gly Lys Leu Phe Thr Pro Leu
                435                 440                 445

Asn Val Asp Ala Ile Glu Glu Ser Pro Ser Lys Glu Pro Lys Pro Val
    450                 455                 460

Gly Leu Asn Asn Lys Glu Arg Phe Arg Thr Ala Phe Arg Met Lys Ala
465                 470                 475                 480

Tyr Ala Phe Trp Gln Ser Ser Glu Asp Ala Gly Thr Gly Asp Pro Met
                485                 490                 495

Ala Glu Asp Arg Gly Tyr Gly Asn Asp Phe Pro Ile Glu Asp Met Ile
                500                 505                 510

Pro Thr Leu Lys Ala Ala Ile Arg Ala Val Arg Ile Leu Gln Phe Arg
    515                 520                 525

Leu Tyr Lys Lys Lys Phe Lys Glu Thr Leu Arg Pro Tyr Asp Val Lys
    530                 535                 540
```

-continued

```
Asp Val Ile Glu Gln Tyr Ser Ala Gly His Leu Asp Met Leu Ser Arg
545                 550                 555                 560

Ile Lys Tyr Leu Gln Thr Arg Ile Asp Met Ile Phe Thr Pro Gly Pro
                565                 570                 575

Pro Ser Thr Pro Lys His Lys Lys Ser Gln Lys Gly Ser Ala Phe Thr
            580                 585                 590

Phe Pro Ser Gln Gln Ser Pro Arg Asn Glu Pro Tyr Val Ala Arg Pro
        595                 600                 605

Ser Thr Ser Glu Ile Glu Asp Gln Ser Met Met Gly Lys Phe Val Lys
    610                 615                 620

Val Glu Arg Gln Val Gln Asp Met Gly Lys Lys Leu Asp Phe Leu Val
625                 630                 635                 640

Asp Met His Met Gln His Met Glu Arg Leu Gln Val Gln Val Thr Glu
                645                 650                 655

Tyr Tyr Pro Thr Lys Gly Thr Ser Ser Pro Ala Glu Ala Glu Lys Lys
                660                 665                 670

Glu Asp Asn Arg Tyr Ser Asp Leu Lys Thr Ile Ile Cys Asn Tyr Ser
            675                 680                 685

Glu Thr Gly Pro Pro Glu Pro Pro Tyr Ser Phe His Gln Val Thr Ile
        690                 695                 700

Asp Lys Val Ser Pro Tyr Gly Phe Phe Ala His Asp Pro Val Asn Leu
705                 710                 715                 720

Pro Arg Gly Gly Pro Ser Ser Gly Lys Val Gln Ala Thr Pro Pro Ser
                725                 730                 735

Ser Ala Thr Thr Tyr Val Glu Arg Pro Thr Val Leu Pro Ile Leu Thr
                740                 745                 750

Leu Leu Asp Ser Arg Val Ser Cys His Ser Gln Ala Asp Leu Gln Gly
            755                 760                 765

Pro Tyr Ser Asp Arg Ile Ser Pro Arg Gln Arg Ser Ile Thr Arg
        770                 775                 780

Asp Ser Asp Thr Pro Leu Ser Leu Met Ser Val Asn His Glu Glu Leu
785                 790                 795                 800

Glu Arg Ser Pro Ser Gly Phe Ser Ile Ser Gln Asp Arg Asp Asp Tyr
                805                 810                 815

Val Phe Gly Pro Asn Gly Gly Ser Ser Trp Met Arg Glu Lys Arg Tyr
                820                 825                 830

Leu Ala Glu Gly Glu Thr Asp Thr Asp Thr Asp Pro Phe Thr Pro Ser
            835                 840                 845

Gly Ser Met Pro Leu Ser Ser Thr Gly Asp Gly Ile Ser Asp Ser Val
        850                 855                 860

Trp Thr Pro Ser Asn Lys Pro Ile
865                 870
```

<210> SEQ ID NO 6
<211> LENGTH: 695
<212> TYPE: PRT
<213> ORGANISM: Homo sapiens

<400> SEQUENCE: 6

```
Met Ala Glu Ala Pro Pro Arg Arg Leu Gly Leu Gly Pro Pro Pro Gly
1               5                   10                  15

Asp Ala Pro Arg Ala Glu Leu Val Ala Leu Thr Ala Val Gln Ser Glu
            20                  25                  30

Gln Gly Glu Ala Gly Gly Gly Ser Pro Arg Arg Leu Gly Leu Leu
        35                  40                  45
```

-continued

```
Gly Ser Pro Leu Pro Pro Gly Ala Pro Leu Pro Gly Pro Gly Ser Gly
    50                  55                  60

Ser Gly Ser Ala Cys Gly Gln Arg Ser Ala Ala His Lys Arg Tyr
65                  70                  75                  80

Arg Arg Leu Gln Asn Trp Val Tyr Asn Val Leu Glu Arg Pro Arg Gly
                85                  90                  95

Trp Ala Phe Val Tyr His Val Phe Ile Phe Leu Leu Val Phe Ser Cys
                    100                 105                 110

Leu Val Leu Ser Val Leu Ser Thr Ile Gln Glu His Gln Glu Leu Ala
            115                 120                 125

Asn Glu Cys Leu Leu Ile Leu Glu Phe Val Met Ile Val Val Phe Gly
    130                 135                 140

Leu Glu Tyr Ile Val Arg Val Trp Ser Ala Gly Cys Cys Cys Arg Tyr
145                 150                 155                 160

Arg Gly Trp Gln Gly Arg Phe Arg Phe Ala Arg Lys Pro Phe Cys Val
                165                 170                 175

Ile Asp Phe Ile Val Phe Val Ala Ser Val Ala Val Ile Ala Ala Gly
                    180                 185                 190

Thr Gln Gly Asn Ile Phe Ala Thr Ser Ala Leu Arg Ser Met Arg Phe
            195                 200                 205

Leu Gln Ile Leu Arg Met Val Arg Met Asp Arg Arg Gly Gly Thr Trp
    210                 215                 220

Lys Leu Leu Gly Ser Val Val Tyr Ala His Ser Lys Glu Leu Ile Thr
225                 230                 235                 240

Ala Trp Tyr Ile Gly Phe Leu Val Leu Ile Phe Ala Ser Phe Leu Val
                245                 250                 255

Tyr Leu Ala Glu Lys Asp Ala Asn Ser Asp Phe Ser Ser Tyr Ala Asp
                    260                 265                 270

Ser Leu Trp Trp Gly Thr Ile Thr Leu Thr Thr Ile Gly Tyr Gly Asp
            275                 280                 285

Lys Thr Pro His Thr Trp Leu Gly Arg Val Leu Ala Ala Gly Phe Ala
    290                 295                 300

Leu Leu Gly Ile Ser Phe Phe Ala Leu Pro Ala Gly Ile Leu Gly Ser
305                 310                 315                 320

Gly Phe Ala Leu Lys Val Gln Glu Gln His Arg Gln Lys His Phe Glu
                325                 330                 335

Lys Arg Arg Met Pro Ala Ala Asn Leu Ile Gln Ala Ala Trp Arg Leu
                    340                 345                 350

Tyr Ser Thr Asp Met Ser Arg Ala Tyr Leu Thr Ala Thr Trp Tyr Tyr
            355                 360                 365

Tyr Asp Ser Ile Leu Pro Ser Phe Arg Glu Leu Ala Leu Leu Phe Glu
    370                 375                 380

His Val Gln Arg Ala Arg Asn Gly Gly Leu Arg Pro Leu Glu Val Arg
385                 390                 395                 400

Arg Ala Pro Val Pro Asp Gly Ala Pro Ser Arg Tyr Pro Pro Val Ala
                405                 410                 415

Thr Cys His Arg Pro Gly Ser Thr Ser Phe Cys Pro Gly Glu Ser Ser
                    420                 425                 430

Arg Met Gly Ile Lys Asp Arg Ile Arg Met Gly Ser Ser Gln Arg Arg
            435                 440                 445

Thr Gly Pro Ser Lys Gln Gln Leu Ala Pro Pro Thr Met Pro Thr Ser
    450                 455                 460
```

```
Pro Ser Ser Glu Gln Val Gly Glu Ala Thr Ser Pro Thr Lys Val Gln
465                 470                 475                 480

Lys Ser Trp Ser Phe Asn Asp Arg Thr Arg Phe Arg Ala Ser Leu Arg
            485                 490                 495

Leu Lys Pro Arg Thr Ser Ala Glu Asp Ala Pro Ser Glu Glu Val Ala
        500                 505                 510

Glu Glu Lys Ser Tyr Gln Cys Glu Leu Thr Val Asp Asp Ile Met Pro
        515                 520                 525

Ala Val Lys Thr Val Ile Arg Ser Ile Arg Ile Leu Lys Phe Leu Val
    530                 535                 540

Ala Lys Arg Lys Phe Lys Glu Thr Leu Arg Pro Tyr Asp Val Lys Asp
545                 550                 555                 560

Val Ile Glu Gln Tyr Ser Ala Gly His Leu Asp Met Leu Gly Arg Ile
                565                 570                 575

Lys Ser Leu Gln Thr Arg Val Asp Gln Ile Val Gly Arg Gly Pro Gly
            580                 585                 590

Asp Arg Lys Ala Arg Glu Lys Gly Asp Lys Gly Pro Ser Asp Ala Glu
        595                 600                 605

Val Val Asp Glu Ile Ser Met Met Gly Arg Val Val Lys Val Glu Lys
    610                 615                 620

Gln Val Gln Ser Ile Glu His Lys Leu Asp Leu Leu Leu Gly Phe Tyr
625                 630                 635                 640

Ser Arg Cys Leu Arg Ser Gly Thr Ser Ala Ser Leu Gly Ala Val Gln
                645                 650                 655

Val Pro Leu Phe Asp Pro Asp Ile Thr Ser Asp Tyr His Ser Pro Val
            660                 665                 670

Asp His Glu Asp Ile Ser Val Ser Ala Gln Thr Leu Ser Ile Ser Arg
        675                 680                 685

Ser Val Ser Thr Asn Met Asp
    690                 695

<210> SEQ ID NO 7
<211> LENGTH: 854
<212> TYPE: PRT
<213> ORGANISM: Homo sapiens

<400> SEQUENCE: 7

Met Lys Asp Val Glu Ser Gly Arg Gly Arg Val Leu Leu Asn Ser Ala
1               5                   10                  15

Ala Ala Arg Gly Asp Gly Leu Leu Leu Gly Thr Arg Ala Ala Thr
            20                  25                  30

Leu Gly Gly Gly Gly Gly Leu Arg Glu Ser Arg Arg Gly Lys Gln
        35                  40                  45

Gly Ala Arg Met Ser Leu Leu Gly Lys Pro Leu Ser Tyr Thr Ser Ser
50                  55                  60

Gln Ser Cys Arg Arg Asn Val Lys Tyr Arg Arg Val Gln Asn Tyr Leu
65                  70                  75                  80

Tyr Asn Val Leu Glu Arg Pro Arg Gly Trp Ala Phe Ile Tyr His Ala
                85                  90                  95

Phe Val Phe Leu Leu Val Phe Gly Cys Leu Ile Leu Ser Val Phe Ser
            100                 105                 110

Thr Ile Pro Glu His Thr Lys Leu Ala Ser Ser Cys Leu Leu Ile Leu
        115                 120                 125

Glu Phe Val Met Ile Val Val Phe Gly Leu Glu Phe Ile Ile Arg Ile
130                 135                 140
```

-continued

```
Trp Ser Ala Gly Cys Cys Cys Arg Tyr Arg Gly Trp Gln Gly Arg Leu
145                 150                 155                 160
Arg Phe Ala Arg Lys Pro Phe Cys Val Ile Asp Thr Ile Val Leu Ile
                165                 170                 175
Ala Ser Ile Ala Val Val Ser Ala Lys Thr Gln Gly Asn Ile Phe Ala
            180                 185                 190
Thr Ser Ala Leu Arg Ser Leu Arg Phe Leu Gln Ile Leu Arg Met Val
        195                 200                 205
Arg Met Asp Arg Arg Gly Gly Thr Trp Lys Leu Leu Gly Ser Val Val
    210                 215                 220
Tyr Ala His Ser Lys Glu Leu Ile Thr Ala Trp Tyr Ile Gly Phe Leu
225                 230                 235                 240
Val Leu Ile Phe Ser Ser Phe Leu Val Tyr Leu Val Glu Lys Asp Ala
                245                 250                 255
Asn Lys Glu Phe Ser Thr Tyr Ala Asp Ala Leu Trp Trp Gly Thr Ile
            260                 265                 270
Thr Leu Thr Thr Ile Gly Tyr Gly Asp Lys Thr Pro Leu Thr Trp Leu
        275                 280                 285
Gly Arg Leu Leu Ser Ala Gly Phe Ala Leu Leu Gly Ile Ser Phe Phe
    290                 295                 300
Ala Leu Pro Ala Gly Ile Leu Gly Ser Gly Phe Ala Leu Lys Val Gln
305                 310                 315                 320
Glu Gln His Arg Gln Lys His Phe Glu Lys Arg Arg Asn Pro Ala Ala
                325                 330                 335
Asn Leu Ile Gln Cys Val Trp Arg Ser Tyr Ala Ala Asp Glu Lys Ser
            340                 345                 350
Val Ser Ile Ala Thr Trp Lys Pro His Leu Lys Ala Leu His Thr Cys
        355                 360                 365
Ser Pro Thr Lys Lys Glu Gln Gly Glu Ala Ser Ser Ser Gln Lys Leu
    370                 375                 380
Ser Phe Lys Glu Arg Val Arg Met Ala Ser Pro Arg Gly Gln Ser Ile
385                 390                 395                 400
Lys Ser Arg Gln Ala Ser Val Gly Asp Arg Arg Ser Pro Ser Thr Asp
                405                 410                 415
Ile Thr Ala Glu Gly Ser Pro Thr Lys Val Gln Lys Ser Trp Ser Phe
            420                 425                 430
Asn Asp Arg Thr Arg Phe Arg Pro Ser Leu Arg Leu Lys Ser Ser Gln
        435                 440                 445
Pro Lys Pro Val Ile Asp Ala Asp Thr Ala Leu Gly Thr Asp Asp Val
    450                 455                 460
Tyr Asp Glu Lys Gly Cys Gln Cys Asp Val Ser Val Glu Asp Leu Thr
465                 470                 475                 480
Pro Pro Leu Lys Thr Val Ile Arg Ala Ile Arg Ile Met Lys Phe His
                485                 490                 495
Val Ala Lys Arg Lys Phe Lys Glu Thr Leu Arg Pro Tyr Asp Val Lys
            500                 505                 510
Asp Val Ile Glu Gln Tyr Ser Ala Gly His Leu Asp Met Leu Cys Arg
        515                 520                 525
Ile Lys Ser Leu Gln Thr Arg Val Asp Gln Ile Leu Gly Lys Gly Gln
    530                 535                 540
Ile Thr Ser Asp Lys Lys Ser Arg Glu Lys Ile Thr Ala Glu His Glu
545                 550                 555                 560
```

```
Thr Thr Asp Asp Leu Ser Met Leu Gly Arg Val Val Lys Val Glu Lys
                565                 570                 575

Gln Val Gln Ser Ile Glu Ser Lys Leu Asp Cys Leu Leu Asp Ile Tyr
            580                 585                 590

Gln Gln Val Leu Arg Lys Gly Ser Ala Ser Leu Ala Leu Ala Ser
        595                 600                 605

Phe Gln Ile Pro Pro Phe Glu Cys Glu Gln Thr Ser Asp Tyr Gln Ser
    610                 615                 620

Pro Val Asp Ser Lys Asp Leu Ser Gly Ser Ala Gln Asn Ser Gly Cys
625                 630                 635                 640

Leu Ser Arg Ser Thr Ser Ala Asn Ile Ser Arg Gly Leu Gln Phe Ile
                645                 650                 655

Leu Thr Pro Asn Glu Phe Ser Ala Gln Thr Phe Tyr Ala Leu Ser Pro
                660                 665                 670

Thr Met His Ser Gln Ala Thr Gln Val Pro Ile Ser Gln Ser Asp Gly
            675                 680                 685

Ser Ala Val Ala Ala Thr Asn Thr Ile Ala Asn Gln Ile Asn Thr Ala
        690                 695                 700

Pro Lys Pro Ala Ala Pro Thr Thr Leu Gln Ile Pro Pro Leu Pro
705                 710                 715                 720

Ala Ile Lys His Leu Pro Arg Pro Glu Thr Leu His Pro Asn Pro Ala
                725                 730                 735

Gly Leu Gln Glu Ser Ile Ser Asp Val Thr Thr Cys Leu Val Ala Ser
            740                 745                 750

Lys Glu Asn Val Gln Val Ala Gln Ser Asn Leu Thr Lys Asp Arg Ser
        755                 760                 765

Met Arg Lys Ser Phe Asp Met Gly Gly Glu Thr Leu Leu Ser Val Cys
    770                 775                 780

Pro Met Val Pro Lys Asp Leu Gly Lys Ser Leu Ser Val Gln Asn Leu
785                 790                 795                 800

Ile Arg Ser Thr Glu Glu Leu Asn Ile Gln Leu Ser Gly Ser Glu Ser
                805                 810                 815

Ser Gly Ser Arg Gly Ser Gln Asp Phe Tyr Pro Lys Trp Arg Glu Ser
            820                 825                 830

Lys Leu Phe Ile Thr Asp Glu Glu Val Gly Pro Glu Thr Glu Thr
        835                 840                 845

Asp Thr Phe Ala Arg Ile
    850

<210> SEQ ID NO 8
<211> LENGTH: 29
<212> TYPE: PRT
<213> ORGANISM: Homo sapiens

<400> SEQUENCE: 8

Lys Lys Glu Gln Gly Glu Ala Ser Ser Asn Lys Phe Cys Ser Asn Lys
1               5                   10                  15

Gln Lys Leu Phe Arg Met Tyr Thr Ser Arg Lys Gln Ser
            20                  25

<210> SEQ ID NO 9
<211> LENGTH: 9
<212> TYPE: PRT
<213> ORGANISM: Homo sapiens

<400> SEQUENCE: 9
```

```
-continued

Lys Lys Glu Gln Gly Glu Ala Ser Ser
1               5

<210> SEQ ID NO 10
<211> LENGTH: 20
<212> TYPE: PRT
<213> ORGANISM: Homo sapiens

<400> SEQUENCE: 10

Asn Lys Phe Cys Ser Asn Lys Gln Lys Leu Phe Arg Met Tyr Thr Ser
1               5                   10                  15

Arg Lys Gln Ser
            20
```

US 6,649,371 B1

POTASSIUM CHANNEL KCNQ5 AND SEQUENCES ENCODING THE SAME

This application claims priority on provisional Application No. 60/139,891 filed on Jun. 22, 1999, the entire contents of which are hereby incorporated by reference.

TECHNICAL FIELD

This invention relates to novel potassium channels and genes encoding these channels. More specifically the invention provides isolated polynucleotides encoding the KCNQ5 potassium channel subunit, cells transformed with these polynucleotides, transgenic animals comprising genetic mutations, and the use of the transformed cells and the transgenic animals for the in vitro and in vivo screening of chemical compounds affecting KCNQ5 subunit containing potassium channels.

BACKGROUND ART

Potassium channels participate in the regulation of electrical signalling in excitable cells, and regulates the ionic composition of biological fluids. Mutations in the four known genes of the KCNQ branch of the $K^+$-channel gene family underlie inherited cardiac arrhythmia's, in some cases associated with deafness, neonatal epilepsy, and the progressive hearing loss of the elderly (presbyacusis).

Ion channels play important roles in signal transduction and in the regulation of the ionic composition of intra- and extracellular fluids. KCNQ1 is a typical member of the voltage-gated potassium channel superfamily with 6 transmembrane domains and a pore region situated between the fifth and the sixth transmembrane domain. The minK protein (also known as KCNE1 or IsK) has a single transmembrane span and cannot form potassium channels on its own. However, as a β-subunit it enhances and modifies currents mediated by KCNQ1. These heteromeric channels participate in the repolarization of the heart action potential. Certain mutations in either KCNQ1 or KCNE1 cause a form of the autosomal dominant long QT syndrome (LQTS), a disease characterised by repolarization anomalies of cardiac action potentials resulting in arrhythmias and sudden death. Interestingly, other mutations in either gene lead to the recessive Jervell and Lange-Nielsen (JLN) syndrome that combines LQTS with congenital deafness. In order to cause deafness, KCNQ1/minK currents must be reduced below levels that are already sufficiently low to cause cardiac arrhythmia.

Mutated and non-mutated KCNQ2 and KCNQ3 potassium channels have been disclosed in WO 99/07832, WO 99/21875 and WO 99/31232.

SUMMARY OF THE INVENTION

We have now cloned and characterised KCNQ5, a novel member of the KCNQ family of potassium channel proteins. KCNQ5 forms heteromeric channels with other KCNQ channel subunits, in particular KCNQ3 and KCNQ4.

The present invention has important implications for the characterisation and exploitation of this interesting branch of the potassium channel super family.

Accordingly, in its first aspect, the invention provides an isolated polynucleotide having a nucleic acid sequence which is capable of hybridising under at least medium stringency conditions with the polynucleotide sequence presented as SEQ ID NO: 1, its complementary strand, or a sub-sequence thereof.

In another aspect the invention provides a recombinantly produced polypeptide encoded by the polynucleotide of the invention.

In a third aspect the invention provides a cell genetically manipulated by the incorporation of a heterologous polynucleotide of the invention.

In a fourth aspect the invention provides a method of screening a chemical compound for inhibiting or activating or otherwise modulating the activity on a potassium channel comprising at least one KCNQ5 channel subunit, which method comprises the steps of subjecting a KCNQ5 channel subunit containing cell to the action of the chemical compound; and monitoring the membrane potential, the current, the potassium flux, or the secondary calcium influx of the KCNQ5 channel subunit containing cell.

In a fifth aspect the invention relates to the use of a polynucleotide sequence of the invention for the screening of genetic materials from humans suffering from neurological diseases for mutations in the KCNQ5 gene.

In a sixth aspect the invention relates to the chemical compound identified by the method of the invention, in particular to the use of such compounds for diagnosis, treatment or alleviation of a disease related to diseases or adverse conditions of the CNS, including affective disorders, Alzheimer's disease, anxiety, ataxia, CNS damage caused by trauma, stroke or neurodegenerative illness, cognitive deficits, compulsive behaviour, dementia, depression, Huntington's disease, mania, memory impairment, memory disorders, memory dysfunction, motion disorders, motor disorders, neurodegenerative diseases, Parkinson's disease and Parkinson-like motor disorders, phobias, Pick's disease, psychosis, schizophrenia, spinal cord damage, stroke, tremor, seizures, convulsions and epilepsy.

In a seventh aspect the invention provides a transgenic animal comprising a knock-out mutation of the endogenous KCNQ5 gene, a replacement by or an additional expression of a mutated KCNQ5 gene, or genetically manipulated in order to over-express the KCNQ5 gene or to over-express mutated KCNQ5 gene.

In an eighth aspect the invention relates to the use of the transgenic animal of the invention for the in vivo screening of therapeutic compounds.

Other objects of the invention will be apparent to the person skilled in the art from the following detailed description and examples.

DETAILED DISCLOSURE OF THE INVENTION

The present invention provides novel potassium channels and genes encoding these channels. The invention also provides cells transformed with these genes, transgenic animals comprising genetic mutations, and the use of the transformed cells and the transgenic animals for the in vitro and in vivo screening of drugs affecting KCNQ5 containing potassium channels.

Polynucleotides

In its first aspect, the invention relates to novel nuceic acid molecules encoding a polypeptide comprising all or a portion of a KCNQ5 protein.

In a preferred embodiment, the polynucleotides of the invention are such which have a nucleic acid sequence capable of hybridising under at least medium stringency conditions with the polynucleotide sequence presented as SEQ ID NO: 1, its complementary strand, or a sub-sequence thereof.

The polynucleotides of the invention include DNA, cDNA and RNA sequences, as well as anti-sense sequences, and include naturally occurring, synthetic, and intentionally manipulated polynucleotides. The polynucleotides of the invention also include sequences that are degenerate as a result of the genetic code.

As defined herein, the term "polynucleotide" refers to a polymeric form of nucleotides of at least 10 bases in length, preferably at least 15 bases in length. By "isolated polynucleotide" is meant a polynucleotide that is not immediately contiguous with both of the coding sequences with which it is immediately contiguous (one on the 5' end and one on the 3' end) in the naturally occurring genome of the organism from which it is derived. The term therefore includes recombinant DNA which is incorporated into an expression vector, into an autonomously replicating plasmid or virus, or into the genomic DNA of a prokaryote or eukaryote, or which exists as a separate molecule, e.g. a cDNA, independent from other sequences.

The polynucleotides of the invention also include allelic variants and "mutated polynucleotides" having a nucleotide sequence that differs from the sequence presented as SEQ ID NO: 1 at one or more nucleotide positions. The mutated polynucleotide may in particular be a polynucleotide of the invention having a nucleotide sequence as in SEQ ID NO: 1, which sequence, however, differs from SEQ ID NO: 1 so as to effect the expression of a variant polypeptide. The mutated polynucleotide may be a polynucleotide of the invention having a nucleotide sequence encoding a potassium channel having an amino acid sequence that has been changed at one or more positions. The mutated polynucleotide may in particular be a polynucleotide of the invention having a nucleotide sequence encoding a potassium channel having an amino acid sequence that has been changed at one or more positions located in the conserved regions, as defined by Table 1, below.

Hybridisation Protocol

The polynucleotides of the invention are such which have a nucleic acid sequence capable of hybridising with the polynucleotide sequence presented as SEQ ID NO: 1, its complementary strand, or a sub-sequence thereof, under at least medium, medium/high, or high stringency conditions, as described in more detail below.

In a preferred embodiment the polynucleotide is a fragment of at least 15 bases in length which is sufficient to permit the fragment to hybridise to DNA that encodes a polypeptide of the invention, preferably the polypeptide having the amino acid sequence presented as SEQ ID NO: 2 under at least medium, medium/high, or high stringency conditions, as described in more detail below.

Suitable experimental conditions for determining hybridisation between a nucleotide probe and a homologous DNA or RNA sequence, involves pre-soaking of the filter containing the DNA fragments or RNA to hybridise in 5×SSC [Sodium chloride/Sodium citrate; cf. Sambrook et al.; *Molecular Cloning: A Laboratory Manual*, Cold Spring Harbor Lab., Cold Spring Harbor, N.Y. 1989] for 10 minutes, and pre-hybridisation of the filter in a solution of 5×SSC, 5×Denhardt's solution [cf. Sambrook et al.; Op cit.], 0.5% SDS and 100 μg/ml of denatured sonicated salmon sperm DNA [cf. Sambrook et al.; Op cit.], followed by hybridisation in the same solution containing a concentration of 10 ng/ml of a random-primed [Feinberg A P & Vogelstein B; *Anal. Biochem.* 1983 132 6–13], $^{32}$P-dCTP-labeled (specific activity >1×10$^9$ cpm/μg) probe for 12 hours at approximately 45° C.

The filter is then washed twice for 30 minutes in 2×SSC, 0.5% SDS at a temperature of at least at least 60° C. (medium stringency conditions), preferably of at least 65° C. (medium/high stringency conditions), more preferred of at least 70° C. (high stringency conditions), and even more preferred of at least 75° C. (very high stringency conditions).

Molecules to which the oligonucleotide probe hybridises under these conditions may be detected using a x-ray film.

DNA Sequence Homology

In a preferred embodiment, the polynucleotides of the invention show a homology of at least 65%, preferably at least 70%, more preferred at least 80%, even more preferred at least 90%, most preferred at least 95%, with the polynucleotide sequence presented as SEQ ID NO: 1.

As defined herein, the DNA sequence homology may be determined as the degree of identity between two DNA sequences indicating a derivation of the first sequence from the second. The homology may suitably be determined by means of computer programs known in the art such as GAP provided in the GCG program package [Needleman S B and Wunsch C D, *Journal of Molecular Biology* 1970 48 443–453] using default parameters suggested herein.

Cloned Polynucleotides

The isolated polynucleotide of the invention may in particular be a cloned polynucleotide.

As defined herein, the term "cloned polynucleotide", refers to a polynucleotide or DNA sequence cloned in accordance with standard cloning procedures currently used in genetic engineering to relocate a segment of DNA, which may in particular be cDNA, i.e. enzymatically derived from RNA, from its natural location to a different site where it will be reproduced.

Cloning may be accomplished by excision and isolation of the desired DNA segment, insertion of the piece of DNA into the vector molecule and incorporation of the recombinant vector into a cell where multiple copies or clones of the DNA segment will be replicated, by reverse transcription of mRNA (reverse transcriptase technology), and by use of sequence-specific oligonucleotides and DNA polymerase in a polymerase chain reaction (PCR technology).

The cloned polynucleotide of the invention may alternatively be termed "DNA construct" or "isolated DNA sequence", and may in particular be a complementary DNA (cDNA).

It is well established that potassium channels may be formed as heteromeric channels, composed of different subunits. Also it has been established that the potassium channel of the invention may form heteromers with other KCNQ's, in particular KCNQ3 and KCNQ4, when co-expressed with these subunits. In addition, potassium channels can associate with non-homologous subunits (β-subunits), e.g. the KCNE1 (also known as mink or lsK), the KCNE2 (also known as the mink-related peptide (MiRP1), the KCNE3 (also known as MiRP2), the KCNE4 (also known as MiRP3), and/or the KCNE5 (also known as KCNE1L) subunit, that co-assemble and functionally modulate these channels or lead to a specific localisation within the cell.

Therefore, in a preferred embodiment, the polynucleotide of the invention is cloned and either expressed by itself or co-expressed with polynucleotides encoding other subunits, in particular a polynucleotide encoding a KCNQ3 channel subunit or a polynucleotide encoding a KCNQ4 channel subunit.

In another aspect of the invention, isolated and purified KCNQ5 antisence oligonucleotides can be made and a method utilised for diminishing the level of expression of KCNQ5 by a cell comprising administering one or more KCNQ5 antisense oligonucleotides. By KCNQ5 antisense oligonucleotides reference is made to oligonucleotides that have a nucleotide sequence that interacts through base pairing with a specific complementary nucleic acid sequence involved in the expression of KCNQ5 such that the expression of KCNQ5 is reduced. Preferably, the nucleic acid sequence involved in the expression of KCNQ5 is a genomic DNA molecule or mRNA molecule that encodes KCNQ5. This genomic DNA molecule can comprise regulatory regions of the KCNQ5 gene, the pre- or pro-portions of the KCNQ5 gene, or the coding sequence for mature KCNQ5 protein.

The term "complementary to a nucleotide sequence" in the context of KCNQ5 antisense oligonucleotides and methods therefor means sufficiently complementary to such a sequence as to allow hybridization to that sequence in a cell, i.e. under physiological conditions. The KCNQ5 antisense oligonucleotides preferably comprise a sequence comprising of from about 8 to about 100 nucleotides, more preferably of from about 15 to about 30 nucleotides.

The KCNQ5 antisense oligonucleotides can also include derivatives which comprise a variety of modifications that confer resistance to nucleolytic degradation such as e.g. modified internucleoside linkages modified nucleic acid bases and/or sugars and the like. Examples of such derivatives include backbone modifications such as phosphotriester, phosphorothioate, methylphosphate, phosphoramidate, phosphorodithioate and formacetal as well as morpholino, peptide nucleic acid analogues and dithioate repeating units.

The usefulness of antisense molecules have been described by e.g. Toulme & Helene, *Gene* 1988 72 51–58; Inouye, *Gene* 1988 72 25–34; Uhlmann & Peyman, *Chemical Reviews* 1990 90 543–584; Robertson, *Nature Biotechnology* 1997 15 209; and Gibbons & Dzau, *Science* 1996 272 689–693, which publications are hereby incorporated by reference.

Biological Sources

The isolated polynucleotide of the invention may be obtained from any suitable human or animal source. In a preferred embodiment, which the polynucleotide of the invention is cloned from, or produced on the basis of a cDNA library, e.g. of the retina, skeletal muscle, or brain, in particular the cerebral cortex, occipital pole, frontal and temporal lobes, putamen and the hippocampus, and in the piriform cortex, the entorhinal cortex, the pontine medulla and the facial nucleus, and in the cerebellum. In a more preferred embodiment, which the polynucleotide of the invention is cloned from, or produced on the basis of a CDNA library of the thalamus. Commercial cDNA libraries are available from e.g. Stratagene and Clontech.

The KCNQ5 gene of the invention has been localised to the long arm of chromosome 6 (6q14).

The isolated polynucleotide of the invention may be obtained methods known in the art, e.g. those described in the working examples below.

Preferred Polynucleotides

In a preferred embodiment, polynucleotide of the invention has the polynucleotide sequence presented as SEQ ID NO: 1.

In another preferred embodiment the polynucleotide of the invention is a sequence giving rise to KCNQ5 channels subunits comprising one or more substitutions.

In another preferred embodiment the polynucleotide of the invention is a sequence giving rise to KCNQ5 channels subunits comprising one or more substitutions in the conserved regions, as defined in more details below.

It has been demonstrated that KCNQ channels often show alternative splicing and therefore may occur as isoforms originating from the same gene. Such isoforms as well as the different cDNA sequences from which they occurred are also contemplated within the scope of the present invention.

Finally the genes encoding KCNQ channel subunits in other species have been found to differ slightly from the human genes. However, genes of other species, e.g. mouse, rat, monkey, rabbit, etc., are also contemplated within the scope of the present invention.

Recombinantly Produced Polypeptides

In another aspect the invention relates to novel KCNQ5 proteins. More specifically, the invention relates to substantially pure functional polypeptides that have the electrophysiological and pharmacological properties of a KCNQ5 channel, or KCNQ5 channel subunits. The novel polypeptides of the invention may be obtained by the polynucleotides of the invention using standard recombinant DNA technology.

In a preferred embodiment, a polypeptide of the invention is the KCNQ5 potassium channel having the amino acid sequence presented as SEQ ID NO: 2, and biologically active fragments hereof.

Modifications of this primary amino acid sequence may result in proteins which have substantially equivalent activity as compared to the unmodified counterpart polypeptide, and thus may be considered functional analogous of the parent proteins. Such modifications may be deliberate, e.g. as by site-directed mutagenesis, or they may occur spontaneous, and include splice variants, isoforms, homologues from other species, and polymorphisms. Such functional analogous are also contemplated according to the invention.

Moreover, modifications of this primary amino acid sequence may result in proteins which do not retain the biological activity of the parent protein, including dominant negative forms, etc. A dominant negative protein may interfere with the wild-type protein by binding to, or otherwise sequestering regulating agents, such as upstream or downstream components, that normally interact functionally with the polypeptide. Such dominant negative forms are also contemplated according to the invention.

In the context of this invention, the term "variant polypeptide" means a polypeptide (or protein) having an amino acid sequence that differs from the sequence presented as SEQ ID NO: 2 at one or more amino acid positions. Such variant polypeptides include the modified polypeptides described above, as well as conservative substitutions, splice variants, isoforms, homologues from other species, and polymorphisms.

As defined herein, the term "conservative substitutions" denotes the replacement of an amino acid residue by another, biologically similar residue. Examples of conservative substitutions include the substitution of one hydrophobic residue such as isoleucine, valine, leucine or methionine for another, or the substitution of one polar residue for another, such as the substitution of arginine for lysine, glutamic for aspartic acid, or glutamine for asparagine, and the like. The term conservative substitution also include the use of a substituted amino acid residue in place of an un-substituted parent amino acid residue provided that antibodies raised to the substituted polypeptide also immune-react with the un-substituted polypeptide.

KCNQ1 Numbering System

In the context of this invention, amino acid residues (as well as nucleic acid bases) are specified using the established one-letter symbol.

By aligning the amino acid sequences of a polypeptide of the present invention to those of the known polypeptides, a specific amino acid numbering system may be employed, by which system it is possible to unambiguously allot an amino acid position number to any amino acid residue in any KNCQ channel protein, which amino acid sequence is known.

Such an alignment is presented in Table 1, below. Using the ClustalX computer alignment program [Thompson J D, Gibson T J, Piewniak F, Jeanmougin F, & Higgins D G: The ClustalX windows interface: flexible strategies for multiple sequence alignment aided by quality analysis tools; *Nucleic Acids Res.* 1997 25 (24) 4876–82], and the default parameters suggested herein, the amino acid sequence of a polypeptide of the present invention (hKCNQ5) and the amino acid sequences of the known polypeptides hKCNQ2–4 are aligned with, and relative to, the amino acid sequences of the known polypeptide hKCNQ1 (also known as KvLQT1). In the context of this invention this numbering system is designated the KCNQ1 Numbering System.

In describing the various enzyme variants produced or contemplated according to the invention, the following nomenclatures have been adapted for ease of reference:

Original Amino Acid/Position/Substituted Amino Acid

According to this nomenclature the substitution of serine for glycine at position 329 of Table 1 is designated as "G329S".

TABLE 1

CLUSTAL X Multiple Sequence Alignment
KCNQ1 Numbering

```
hKCNQ1   MAAASSPPRA E-----RKRW GWGRLPGARR GSAGLAKKCP FSLELAEGG- ---P--AGGA    60
hKCNQ2   MVQKSR---- ---------- NGGVYPGPSG EKKLKVG--- -FVGLDPG-- -------APD
hKCNQ3   MGLKARRAAG AAGGGGDGGG GGGGAANPAG GDAAAAGDEE RKVGLAPGDV EQVTLALGAG
hKCNQ4   MAEAPPRR-- ---------L GLGPPPGDAP RAELVALT-- -AVQSEQGE- -------AGG
hKCNQ5   MKDVES---- ---------- GRGRVLLNSA AARGDGLLLL GTRAATLGG- -------GGG
         *                    *                    * hKCNQ1   LYAPIAPGAP GPAPPASPAA PAAPPVASDL GPRPPVSLDP RVSIYSTRRP VLARTHVQGR   120
hKCNQ2   STRDGALLIA G-----SEAP KRGSILSKPR AGGAGAGKPP KRN-AFYRK- ------LQNF
hKCNQ3   ADKDGTLLLE GGG---RDEG QRRTPQGIGL LAKTPLSRPV KRNNAKYRR- ------IQTL
hKCNQ4   GGSPRRLGLL G-----SPLP PGAPLPGPGS GSGSACGQRS SAAHKRYRR- ------LQNW
hKCNQ5   GLRESRRGKQ G--------- ARMSLLGKPL SYTS--SQSC RRN-VKYRR- ------VQNY
                  *                    *                *         * hKCNQ1   VYNFLERPTG WKCFVYHFAV FLIVLVCLIF SVLSTIEQYA ALATGTLFWM EIVLVVFFGT   180
hKCNQ2   LYNVLERPRG W-AFIYHAYV FLLVFSCLVL SVFSTIKEYE KSSEGALYIL EIVTIVVFGV
hKCNQ3   IYDALERPRG W-ALLYHALV FLIVLGCLIL AVLTTFKEYE TVSGDWLLLL ETFAIFIFGA
hKCNQ4   VYNVLERPRG W-AFVYHVFI FLLVFSCLVL SVLSTIQEHQ ELANECLLIL EFVMIVVFGL
hKCNQ5   LYNVLERPRG W-AFIYHAFV FLLVFGCLIL SVFSTIPEHT KLASSCLLIL EFVMIVVFGL
          * **** * *       **    ** * **     * *           *      *     **
                                     Site 1                 Site 2 hKCNQ1   EYVVRLWSAG CRSKYVGLWG RLRFARKPIS IIDLIVVVAS MVVLCVGSKG QVFATSAIRG   240
hKCNQ2   EYFVRIWAAG CCCRYRGWRG RLKFARKPFC VIDIMVLIAS IAVLAAGSQG NVFATSALRS
hKCNQ3   EFALRIWAAG CCCRYKGWRG RLKFARKPLC MLDIFVLIAS VPVVAVGNQG NVLATS-LRS
hKCNQ4   EYIVRVWSAG CCCRYRGWQG RFRFARKPFC VIDFIVFVAS VAVIAAGTQG NTFATSALRS
hKCNQ5   EFIIRIWSAG CCCRYRGWQG RLRFARKPFC VIDTIVLIAS IAVVSAKTQG NIFATSALRS
         *   * * **  *    * * *   * *****    * ** **    *       *   *** *
                                    Site 3                      Site hKCNQ1   IRFLQILRML HVDRQGGTWR LLGSVVFIHR QELITTLYIG FLGLIFSSYF VYLAEKDAVN   300
hKCNQ2   LRFLQILRMI RMDRRGGTWK LLGSVVYAHS KELVTAWYIG FLCLILASFL VYLAEK----
hKCNQ3   LRFLQILRML RMDRRGGTWK LLGSAICAHS KELITAWYIG FLTLILSSFL VYLVEKDVPE
hKCNQ4   MRFLQILRMV RMDRRGGTWK LLGSVVYAHS KELITAWYIG FLVLIFASFL VYLAEKD---
hKCNQ5   LRFLQILRMV RMDRRGGTWK LLGSVVYAHS KELITAWYIG FLVLIFSSFL VYLVEKD---
          ******     ** ****  ****   *   ** * *** ** **   *** **
         4                                      Site 5 hKCNQ1   -----ESGRV EFGSYADALW WGVVTVTTIG YGDKVPQTWV GKTIASCFSV FAISFFALPA   360
hKCNQ2   ----GE--ND HFDTYADALW WGLITLTTIG YGDKYPQTWN GRLLAATFTL IGVSFFALPA
hKCNQ3   VDAQGEEMKE EFETYADALW WGLITLATIG YGDKTPKTWE GRLIAATFSL IGVSFFALPA
hKCNQ4   -------ANS DFSSYADSLW WGTITLTTIG YGDKTPHTWL GRVLAAGFAL LGISFFALPA
hKCNQ5   -------ANK EFSTYADALW WGTITLTTIG YGDKTPLTWL GRLLSAGFAL LGISFFALPA
                *  ** ** **   *  *** **** * **   *        *******
                             P-loop                        Site 6 hKCNQ1   GILGSGFALK VQQKQRQKHF NRQIPAAASL IQTAWRCYAA E---NPDSST WKIYIRKAP-   420
hKCNQ2   GILGSGFALK VQEQHRQKHF EKRRNPAAGL IQSAWRFYAT NLSRTDLHST WQYYERTVT-
hKCNQ3   GILGSGLALK VQEQHRQKHF EKRRKPAAEL IQAAWRYYAT NPNRIDLVAT WRFYESVVS-
hKCNQ4   GILGSGFALK VQEQHRQKHF EKRRMPAANL IQAAWRLYST DMSRAYLTAT WYYYDSILPS
hKCNQ5   GILGSGFALK VQEQHRQKHF EKRRNPAANL IQCVWRSYAA D-EKSVSIAT WKPHLKALHT
         **** *    *             *  ** *            * * hKCNQ1   -------RSH TLLS------ PSPKPK---- ---------- ---------- ------KSVW   480
hKCNQ2   -------VPM YRLIPP--LN QLELLRNLKS KSGLAFRK-- -------DPP PEPSPSQKVS
hKCNQ3          FPF FRKE------ QLEAAS---- ---------- ---------- ---S--QKLG
```

TABLE 1-continued

CLUSTAL X Multiple Sequence Alignment
KCNQ1 Numbering

```
hKCNQ4    FRELALLFEH VQRARNGGLR PLEVRRAPVP DGAPSRYPPV ATCHRPGSTS FCPGESSRMG
hKCNQ5    -------CSP TKKE------ QGEASS---- ---------- ---------- -----SQKLS
                    -          Alternatively Spliced                   - hKCNQ1    KKKKFKLDKD NGVTPGEKML TVPH-ITCDP PEERRLDHFS VDGYDSSVRK SPTLLEVS-M    540
hKCNQ2    LKDRV-FSSP RGVAAKGKGS PQAQTVRRSP SADQSLED-- ---SPSKVPK SWSFGDRSRA
hKCNQ3    LLDRVRLSNP RGSNTKGK-- ------LFTP LNVDAIEE-- ---SPSKEPK PVGLNNKERF
hKCNQ4    IKDRIRMGSS QRRTGPSKQQ LAPPTMPTSP SSEQVGEAT- ---SPTKVQK SWSFNDRTRF
hKCNQ5    FKERVRHASP RGQSIKSRQA SVGD--RRSP STDITAEG-- ---SPTKVQK SWSFNDRTRF
                                  *                          * hKCNQ1    PHFMRTNS-- ----FAEDLD LEGETLLTPI TH-----ISQ LREHHRATIK VIRRMQYFVA    600
hKCNQ2    RQAFRIKGAA S-RQNSEEAS LPGEDIVDDK SCPCEFVTED LTPGLKVSIR AVCVMRFLVS
hKCNQ3    RTAFRMKAYA F-WQSSEDAG T-GDPMAEDR GYGNDFPIED MIPTLKAAIR AVRILQFRLY
hKCNQ4    RASLRLKP-- --RTSAEDAP S--EEVAEEK SYQCELTVDD IMPAVKTVIR SIRILKFLVA
hKCNQ5    RPSLRLKSSQ PKPVIDADTA LGTDDVYDEK GCQCDVSVED LTPPLKTVIR AIRINKFHVA
              *                                * hKCNQ1    KKKFQQARKP YDVRDVIEQY SQGHLNLMVR IKELQRRLDQ SIGK-PSLFI SVS--EKS--    660
hKCNQ2    KRKFKESLRP YDVMDVIEQY SAGHLDMLSR IKSLQSRVDQ IVGRGPAITD KDR--TKG--
hKCNQ3    KKKFKETLRP YDVKDVIEQY SAGHLDMLSR IKYLQTRIDM IFTPGPPSTP KHKKSQKGSA
hKCNQ4    KRKFKETLRP YDVKDVIEQY SAGHLDMLGR IKSLQTRVDQ IVGRGPGDRK AREKGDKG--
hKCNQ5    KRRFKETLRP YDVKDVIEQY SAGHLDMLCR IKSLQTRVDQ ILGKGQITSD KKSREKIT--
          * **      * *** ****** * ***     * ** ** *   *
                  A-domain hKCNQ1    ---------- ---------K DRG--SNTIG ARLNRVEDKV TQLDQRLALI TDMLHQLLSL    720
hKCNQ2    ---------- -------PAE AELPEDPSMM GRLGKVEKQV LSMEKKLDFL VNIYMQRMGI
hKCNQ3    FTFPSQQSPR NEPYVARPST SEI-EDQSMM GKFVKVERQV QDMGKKLDFL VDMHMQHMER
hKCNQ4    ---------- -------PSD AEVVDEISMM GRVVKVEKQV QSIEHKLDLL LGFYSRCLRS
hKCNQ5    ---------- --------AE HETTDDLSNL GRVVKVEKQV QSIESKLDCL LDIYQQVLRK
                                            ** *       * hKCNQ1    HGGSTPG--- SGGPPREGG- -AHITQPCGS G--GSVDPEL FLPSNTLPTY EQLTVP-RRG    780
hKCNQ2    PPTETE---- AYFGAKEPEP APPYHSPEDS REHVDRHGCI VKIVRSSSST GQKNF----S
hKCNQ3    LQVQVT---- EYYPTKGTSS PAEAEKKEDN R-YSDLKTII CNYSETGPGE PPYSFH-QVT
hKCNQ4    GTSASLGA-- VQVPLFDPDI TSDYHSPVDH E-DISVSAQT LSISRSVSTN MD--------
hKCNQ5    GSASALALAS FQIPPFECEQ TSDYQSPVDS KDLSGSAQNS GCLSRSTSAN ISRGLQFILT hKCNQ1    PDEGS----- ---------- ---------- ---------- ---------- ----------    840
hKCNQ2    APPAAPPVQC PPSTSWQPQS HPRQGH---- ---------- ---GTSPVGD HGSLVRIPPP
hKCNQ3    IDKVSPYGFF AHDPVNLPRG GPSSGKV--- ---------- ---QATPPSS ATTYVERPTV
hKCNQ4    ---------- ---------- ---------- ---------- ---------- ----------
hKCNQ5    PNEFSAQTFY ALSPTMHSQA TQVPISQSDG SAVAATNTIA NQINTAPKPA APTTLQIPPP hKCNQ1    ---------- ---------- ---------- ---------- ---------- ----------    900
hKCNQ2    PAHERSLSAY GGGN-RASME FLRQEDTPGC R-PPEGTLRD SDTSISIPSV DHEELERSFS
hKCNQ3    LPILTLLDSR VSCH-SQADL QGPYSDRISP R-QRRSITRD SDTPLSLMSV NHEELERSPS
hKCNQ4    ---------- ---------- ---------- ---------- ---------- ----------
hKCNQ5    LPAIKHLPRP ETLHPNPAGL QESISDVTTC LVASKENVQV AQSNLTKDRS NRKSFDNGGE hKCNQ1    ---------- ---------- ---------- ---------- ---------- ----------    960
hKCNQ2    GFSISQSKEN LDALNSCYAA VAPCAKVRPY IAEGESDTD- -----SDLCTP CGPPPRSATG
hKCNQ3    GFSISQDRDD YVFGPNGGSS WM---REKRY LAEGETDTD- ----TDPFTP SGSMPLSSTG
hKCNQ4    ---------- ---------- ---------- ---------- ---------- ----------
hKCNQ5    TLLSVCPNVP KDLGKSLSVQ NLIRSTEELN IQLSGSESSG SRGSQDFYPK WRESKLFITD hKCNQ1    ---------- ------                                                   976
hKCNQ2    EGPFGDVGWA GPRK--
hKCNQ3    DG-ISDSVWT PSNKPI
hKCNQ4    ---------- ------
hKCNQ5    EEVQPEETET DTFARI
``` hKCNQ1: Human KCNQ1 [Wang, Q et al.; Nature Genet. 1996 12 17–23] (SEQ ID NO: 3)
hKCNQ2: Human KCNQ2 [Biervert et al.; Science 1998 279 403–406] (SEQ ID NO: 4)
hKCNQ3: Human KCNQ3 [Schroeder et al.; Nature 1998 396 687–690] (SEQ ID NO: 5)
hKCNQ4: Human KCNQ4 [Kubisch et al.; Cell 1999 96 (3) 437–46] (SEQ ID NO: 6)
hKCNQ5: Human KCNQ5; A protein of the invention (SEQ ID NO: 7)
- No amino acid in this position.
* Indicates positions which holds a single, fully conserved residue (Conserved regions).

Preferred variants are the splice variants at positions 432–476 (KCNQ1 Numbering) holding the following amino acid residues:

```
1) KKE------ QGEASS---- ------NKFC SNKQKLFRMY TSRKQS; (SEQ ID NO: 8)

2) KKE------ QGEASS---- ---------- ---------- ------; (SEQ ID NQ: 9)

3) --------- ---------- ---------- ---------- ------; or

4) --------- ---------- ------NKFC SNKQKLFRMY TSRKQS. (SEQ ID NO: 10)
```

Another preferred variants is G329S (KCNQ1 numbering), or KCNQ5/G278S ("KCNQ5 numbering").

Biological Activity

Ion channels are excellent targets for drugs. The polynucleotide of the invention encodes a potassium channel, which has been termed KNCQ5.

KCNQ5, or heteromeric channels containing the KCNQ5 subunit, may be a particularly interesting target for the treatment of diseases or adverse conditions of the CNS, including affective disorders, Alzheimer's disease, anxiety, ataxia, CNS damage caused by trauma, stroke or neurodegenerative illness, cognitive deficits, compulsive behaviour, dementia, depression, Huntington's disease, learning deficiencies, mania, memory impairment, memory disorders, memory dysfunction, motion disorders, motor disorders, motor neuron doseases, myokymia, neurodegenerative diseases, Parkinson's disease and Parkinson-like motor disorders, phobias, Pick's disease, psychosis, schizophrenia, seizures, incl. epileptic seizures, spinal cord damage, stroke, tremor, seizures, convulsions and epilepsy.

The novel polynucleotides of the invention may in itself be used as a therapeutic or diagnostic agent. For gene therapy, the person skilled in the art may use sence or antisense nucleic acid molecules as therapeutic agents for KCNQ-related indications.

Heteromers Formed by KCNQ Subunits

The KCNQ channels described so far function physiologically as heteromers. KCNQ1 associates with KCNE1 (also known as minK or lsK); KCNQ2 and KCNQ3 form heteromeric channels that underlie the M-current, an important determinant of neuronal excitability that is regulated by several neurotransmitters, and KCNQ4 is supposed to combine with KCNQ3 to mediate the $I_M$-like current in the outer hair cells.

Like other KCNQ channel subunits, KCNQ5 may interact with other subunits, e.g. KCNE1 or other KCNQ channel subunits, and in particular with KCNQ3, and with KCNQ4. Currents from homomeric KCNQ3 are very small and often cannot be distinguished from Xenopus oocyte background currents. Co-expression of KCNQ3 with KCNQ5 markedly increased current amplitudes. Co-expression of KCNQ4 with KCNQ5 markedly decreased current amplitudes.

Antibodies

The polypeptides of the invention can be used to produce antibodies which are immunoreactive or bind to epitopes of these polypeptides. Polyclonal antibodies which consist essentially of pooled monoclonal antibodies with different specificities, as well as distinct monoclonal antibody preparations may be provided. Polyclonal antibodies which are made up of pooled monoclonal antibodies with different specificities, as well as distinct monoclonal antibody preparations may be provided.

The preparation of polyclonal and monoclonal antibodies is well known in the art. Polyclonal antibodies may in particular be obtained as described by e.g. Green et al.: "Production of Polyclonal Antisera" in *Immunochemical Protocols* (Manson, Ed.); Humana Press, 1992, Pages 1–5; Coligan et al.: "Production of Polyclonal Antisera in rabbits, rats, Mice and Hamsters" in *Current Protocols in Immunology*, 1992, Section 2.4.1; and Ed Harlow and David Lane (Eds.) in "Antibodies; A laboratory manual", Cold Spring Harbor Lab. Press 1988; which protocols are hereby incorporated by reference.

Monoclonal antibodies may in particular be obtained as described by e.g. Kohler & Milstein, Nature 1975 256 495; Coligan et al. in *Current Protocols in Immunology*, 1992, Sections 2.5.1–2.6.7; Harlow et al. in *Antibodies: A Laboratory Manual*; Cold Spring Harbor Pub., 1988, Page 726; which protocols are hereby incorporated by reference.

Briefly, monoclonal antibodies may be obtained by injecting e.g. mice with a composition comprising an antigen, verifying the presence of antibody production by removing a serum sample, removing the spleen to obtain B lymphocytes, fusing the B lymphocytes with myeloma cells to produce hybridomas, cloning the hybridomas, selecting positive clones that produce the antibodies to the antigen, and isolating the antibodies from the hybridoma cultures.

Monoclonal antibodies can be isolated and purified from hybridoma cultures by a variety of well-established techniques, including affinity chromatography with protein A Sepharose, size-exclusion chromatography, and ion-exchange chromatography, see. e.g. Coligan et al. in *Current Protocols in Immunology*, 1992, Sections 2.7.1–2.7.12, and Sections 2.9.1–2.9.3; and Bames et al.: "Purification of Immunoglobulin G (IgG)" in *Methods in Molecular Biology*; Humana Press, 1992, Vol. 10, Pages 79–104.

The polyclonal or monoclonal antibodies may optionally be further purified, e.g. by binding to and elution from a matrix to which the polypeptide, to which the antibodies were raised, is bound.

Antibodies which bind to the polypeptide of the invention can be prepared using an intact polypeptide or fragments containing small peptides of interest as the immunising antigen. The polypeptide used to immunise an animal may be obtained by recombinant DNA techniques or by chemical synthesis, and may optionally be conjugated to a carrier protein. Commonly used carrier proteins which are chemically coupled to the peptide include keyhole limpet hemocyanin (KLH), thyroglobulin, bovine serum albumin (BSA), and tetanus toxoid. The coupled peptide may then be used to immunise the animal, which may in particular be a mouse, a rat, a hamster or a rabbit.

Genetically Manipulated Cells

In a third aspect the invention provides a cell genetically manipulated by the incorporation of the heterologous polynucleotide of the invention. The cell of the invention may in particular be genetically manipulated to transiently or stably express, over-express or co-express a KCNQ5 channel subunit as defined above. Methods of transient and stable transfer are known in the art.

The polynucleotide of the invention may be inserted into an expression vector, e.g. a plasmid, virus or other expression vehicle, and operatively linked to expression control sequences by ligation in a way that expression of the coding sequence is achieved under conditions compatible with the expression control sequences. Suitable expression control sequences include promoters, enhancers, transcription terminators, start codons, splicing signals for introns, and stop codons, all maintained in the correct reading frame of the polynucleotide of the invention so as to permit proper translation of mRNA. Expression control sequences may also include additional components such as leader sequences and fusion partner sequences.

The promoter may in particular be a constitutive or an inducible promoter. When cloning in bacterial systems, inducible promoters such as pL of bacteriophage γ, plac, ptrp, ptac (ptrp-lac hybrid promoter), may be used. When cloning in mammalian systems, promoters derived from the genome of mammalian cells, e.g. the TK promoter or the metallothionein promoter, or from mammalian viruses, e.g. the retrovirus long terminal repeat, the adenovirus late promoter or the vaccinia virus 7.5K promoter, may be used. Promoters obtained by recombinant DNA or synthetic techniques may also be used to provide for transcription of the polynucleotide of the invention.

Suitable expression vectors typically comprise an origin of expression, a promoter as well as specific genes which allow for phenotypic selection of the transformed cells, and include vectors like the T7-based expression vector for expression in bacteria [Rosenberg et al; *Gene* 1987 56 125], the pMSXND expression vector for expression in mammalian cells [Lee and Nathans, *J. Biol. Chem.* 1988 263 3521], baculovirus derived vectors for expression in insect cells, and the oocyte expression vector PTLN [Lorenz C, Pusch M & Jentsch T J: Heteromultimeric CLC chloride channels with novel properties; *Proc. Natl. Acad. Sci. USA* 1996 93 13362–13366].

In a preferred embodiment, the cell of the invention is an eukaryotic cell, in particular a mammalian cell, an oocyte, or a yeast cell. In a more preferred embodiment, the cell of the invention is a human embryonic kidney (HEK) cell, a HEK 293 cell, a BHK21 cell, a Chinese hamster ovary (CHO) cell, a *Xenopus laevis* oocyte (XLO) cell, a COS cell, or any other cell line able to express KCNQ potassium channels.

When the cell of the invention is an eukaryotic cell, incorporation of the heterologous polynucleotide of the invention may be in particular be carried out by infection (employing a virus vector), by transfection (employing a plasmid vector), or by calcium phosphate precipitation, microinjection, electroporation, lipofection, or other physical-chemical methods known in the art.

In a further preferred embodiment, the cell of the invention is genetically manipulated to co-express KCNQ5 and KCNQ1 channel subunits; KCNQ5 and KCNQ2 channel subunits; KCNQ5 and KCNQ3 channel subunits; KCNQ5 and KCNQ4 channel subunits; KCNQ5 and KCNQ1 and KCNQ2 channel subunits; KCNQ5 and KCNQ1 and KCNQ3 channel subunits; KCNQ5 and KCNQ2 and KCNQ3 channel subunits; KCNQ5 and KCNQ1 and KCNQ4 channel subunits; KCNQ5 and KCNQ2 and KCNQ4 channel subunits; KCNQ5 and KCNQ3 and KCNQ4 channel subunits; KCNQ5 and KCNQ1 and KCNQ2 and KCNQ3 channel subunits; KCNQ5 and KCNQ1 and KCNQ2 and KCNQ4 channel subunits; KCNQ5 and KCNQ1 and KCNQ3 and KCNQ4 channel subunits, or KCNQ5 and KCNQ2 and KCNQ3 and KCNQ4 channel subunits.

In another preferred embodiment, membrane preparations are provided. The membrane preparations of the invention may typically be used for screening purposes, and may be obtained by standard techniques.

In a preferred embodiment, frozen intact cells of the invention are homogenised while in cold water suspension and a membrane pellet is collected after centrifugation. The pellet may then be washed in cold water and dialysed to remove endogenous ligands that could compete for binding in the assays. The dialysed membranes may be used as such, or after storage in lyophilised form.

KCNQ5 Active Chemical Compounds

In another aspect the invention relates to chemical compounds capable of binding to, and showing activity at potassium channels containing one or more KCNQ5 subunits. In the context of this invention such compounds are termed KCNQ5 active compounds.

The KCNQ5 active compounds of the invention have therapeutic potential, and may be used for the manufacture of pharmaceutical compositions.

The KCNQ5 active compounds of the invention may in particular be used in diagnosis, treatment, prevention or alleviation of diseases related to diseases or adverse conditions of the CNS, including affective disorders, Alzheimer's disease, anxiety, ataxia, CNS damage caused by trauma, stroke or neurodegenerative illness, cognitive deficits, compulsive behaviour, dementia, depression, Huntington's disease, mania, memory impairment, memory disorders, memory dysfunction, motion disorders, motor disorders, neurodegenerative diseases, Parkinson's disease and Parkinson-like motor disorders, phobias, Pick's disease, psychosis, schizophrenia, spinal cord damage, stroke, tremor, seizures, convulsions and epilepsy.

Currently two compounds have been identified. As a preferred embodiment the invention therefore provides 1,3-dihydro-1-phenyl-3,3-bis-(4-pyridylmethyl)-2H-indol-2-one (Linopirdine) and 10,10-bis-(4-pyridinyl-methyl)-9-(10H)-antracenone (XE991) for use in the manufacture of a pharmaceutical composition for the diagnosis, treatment, prevention or alleviation of the above diseases.

Screening of Drugs

In a further aspect the invention provides methods for screening for KCNQ5 active compounds, i.e. chemical compounds capable of binding to, and showing activity at potassium channels containing one or more KCNQ5 subunits. The activity determined may be inhibitory activity, stimulating activity, or other modulatory activity. In particular the KCNQ5 active compound may induce a second messenger response, which cause a change of the molecular characteristics of the cell, e.g. the ion flux, enzyme activation, changes in the level of intracellular $Ca^{2+}$ or $H^+$, changes cyclic nucleotides such as cAMP, cADP, cGMP, and cGDP, etc.

Therefore, in another aspect, the invention provides a method for identifying functional ligands for a human potassium channel, comprising a KCNQ5 subunit, which method comprises transfecting cells with one or more polypeptides of the invention, encoding a KCNQ5 channel subunit, and detecting the effect on the signal transduction pathway caused in these cells by binding of the ligands to the receptor by a reporter system.

Such chemical compounds can be identified by one of, or both methods described below.

Binding Studies

Binding studies are usually carried out by subjecting the target to binding with a labelled, selective agonist (binding agent), to form a labelled complex, followed by determination of the degree of displacement caused by the test compound upon addition to the complex.

In a specific aspect the invention provides a method of screening a chemical compound for capability of binding to a potassium channel comprising at least one KCNQ5 channel subunit, which method comprises the steps of (i) subjecting a KCNQ5 channel subunit containing cell to the action of a KCNQ5 binding agent to form a complex with the KCNQ5 channel subunit containing cell; (ii) subjecting the complex of step (i) to the action of the chemical compound to be tested; and (iii) detecting the displacement of the KCNQ5 binding agent from the complex with the KCNQ5 channel subunit containing cell.

The KCNQ5 channel subunit containing cell preferably is a cell of the invention as described above.

The KCNQ5 binding agent preferably is a radioactively labelled 1,3-dihydro-1-phenyl-3,3-bis-(4-pyridylmethyl)-2H-indol-2-one (Linopirdine); or 10,10-bis-(4-pyridinyl-methyl)-9-(1OH)-antracenone (XE991).

In a even more preferred embodiment, the binding agent is labelled with $^3H$, and the displacement of the KCNQ5 binding agent from the complex with the KCNQ5 channel subunit containing cell is detected by measuring the amount of radioactivity by conventional liquid scintillation counting.

Activity Studies

The KCNQ5 channel agonists may affect the potassium channel in various ways. The agonist may in particular show inhibitory activity, stimulating activity, or other modulatory activity.

In a specific aspect the invention provides a method for determining the activity at potassium channels containing one or more KCNQ5 subunits. According to this method a KCNQ5 channel subunit containing cell is subjecting to the action of the chemical compound to be tested, and the activity is detected by way of monitoring the membrane potential, the current, the potassium flux, or the secondary calcium influx of the KCNQ5 channel subunit containing cell, preferably a genetically manipulated as described above.

The membrane potential and the current may be monitored by electrophysiologic methods, including patch clamp techniques, such as current clamp technology and two-electrode voltage clamp technology, or by spectroscopic methods, such as fluorescence methods.

In a preferred embodiment, monitoring of the membrane potential of the KCNQ5 channel subunit containing cell is performed by patch clamp techniques.

In another preferred embodiment, monitoring of the membrane potential of the KCNQ5 channel subunit containing cell is performed by spectroscopic methods, e.g. using fluorescence methods. In a more specific embodiment, the KCNQ5 channel subunit containing cell is mixed with a membrane potential indicating agent, that allow for a determination of changes in the membrane potential of the cell, caused by the addition of the test compound. The membrane potential indicating agent may in particular be a fluorescent indicator, preferably $DIBAC_4(3)$, $DiOC5(3)$, and $DiOC2(3)$.

In yet a preferred embodiment, monitoring of the membrane potential of the KCNQ5 channel subunit containing cell is performed by spectroscopic methods, e.g. using a FLIPR assay (Fluorescence Image Plate Reader; available from Molecular Devices).

Screening of Genetic Material

In a further aspect the invention relates to the use of a polynucleotide sequence of the invention for the screening of genetic materials. By this method, individuals bearing a gene identical or homologous to a polynucleotide of the invention may be identified.

In the screening method of the invention, a polynucleotide of the invention, or any fragment or sub-sequence hereof, is employed. For the identification of individuals bearing mutated genes preferably the mutated forms of the polynucleotide represented by SEQ ID NO: 1 are employed.

In the screening method of the invention only short sequences needs to be employed depending on the actual method used. For SSCA, several hundreds of base pairs may be needed, for oligonucleotide or PCR hybridisation only of from about 10 to about 50 basepairs may be needed.

The screening may be accomplished by conventional methods, including hybridisation, SSCA analysis, and microarray technology (DNA chip technology). The hybridisation protocol described above represents a suitable protocol for use in a screening method of the invention.

Transgenic Animals

Transgenic animal models provide the means, in vivo, to screen for therapeutic compounds. Since KCNQ5 is expressed also in brain, they may be helpful in screening for drugs effective in CNS disorders, e.g. epilepsy.

By transgene is meant any piece of polynucleotide which is inserted by artifice into a cell, and thus becomes part of the genome of the organism that develops from that cell. Such a transgene may include a gene which is partly or entirely heterologous (i.e. foreign) to the transgenic organism, or it may represent a gene homologous to an endogenous gene of the organism.

By a transgenic animal is meant any organism holding a cell which includes a polynucleotide sequence which is inserted into that cell by artifice, and which cell becomes part of the transgenic organism which develops from that cell. Such a transgene may be partly or entirely heterologous to the transgenic animal. Although transgenic mice represent a preferred embodiment of the invention, other transgenic mammals including, but not limited to transgenic rodents (e.g. hamsters, guinea pigs, rabbits and rats), and transgenic pigs, cattle, sheep and goats may be created by standard techniques and are included in the invention.

Preferably, the transgene is inserted by artifice into the nuclear genome.

Knock-out and Knock-in Animals

The transgenic knock-out animal models may be developed by homologous recombination of embryonic stem cells with constructs containing genomic sequence from the KCNQ5 gene, that lead to a loss of function of the gene after insertion into the endogenous gene.

By knock-out mutation is meant an alteration in the polynucleotide sequence that reduces the biological activity of the polypeptide normally encoded therefrom. In order to create a true knock-out model, the biological activity of the expressed polypeptide should be reduced by at least 80% relative to the un-mutated gene. The mutation may in particular be a substitution, an insertion, a deletion, a frame-shift mutation, or a mis-sense mutation. Preferably the mutation is a substitution, an insertion or a deletion.

To further assess the role of KCNQ5 at an organism level, the generation of an animal, preferably a mouse, lacking the intact KCNQ5 gene, or bearing a mutated KCNQ5 gene, is desired.

A replacement-type targeting vector, which may be used to create a knock-out model, may be constructed using an isogenic genomic clone, e.g. from a mouse strain such as 129/Sv (Stratagene Inc., La Jolla, Calif.). The targeting vector may be introduced into a suitably-derived line of embryonic stem (ES) cells by electroporation to generate ES cell lines that carry a profoundly truncated form of the KCNQ5 gene. The targeted cell lines may then be injected into a mouse blastula stage embryo to generate chimeric founder mice. Heterozygous offspring may be interbred to homozygosity.

Animal models for over-expression may be generated by integrating one or more polynucleotide sequence of the invention into the genome according to standard techniques.

The procedures disclosed herein involving the molecular manipulation of nucleic acids are known to those skilled in the art, and are described by e.g. Fredrick M A et al. [Fredrick M A et al.: *Short Protocols in Molecular Biology*; John Wiley and Sons, 1995] and Sambrook et al. [Sambrook et al.: *Molecular Cloning: A Laboratory Manual*; 2. Ed., Cold Spring Harbor Lab.; Cold Spring Harbor, N.Y. 1989], and in Alexandra L J (Ed.): *Gene Targeting: A practical approach*; Oxford University Press (Oxford, New York, Tokyo), 1993.

BRIEF DESCRIPTION OF THE DRAWINGS

The present invention is further illustrated by reference to the accompanying drawing, in which.

Figure 7A:
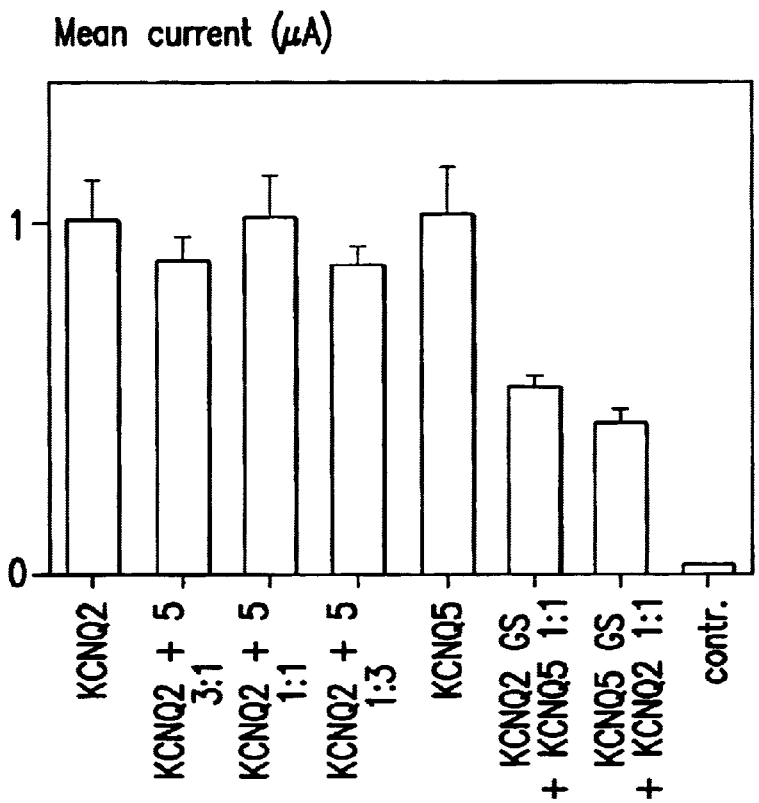
Figure 7B:
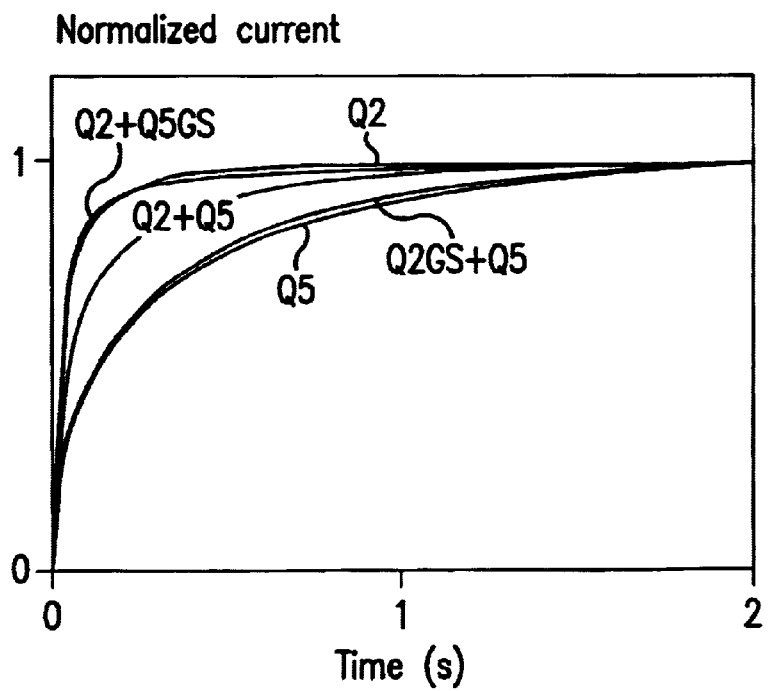
Figure 7C:
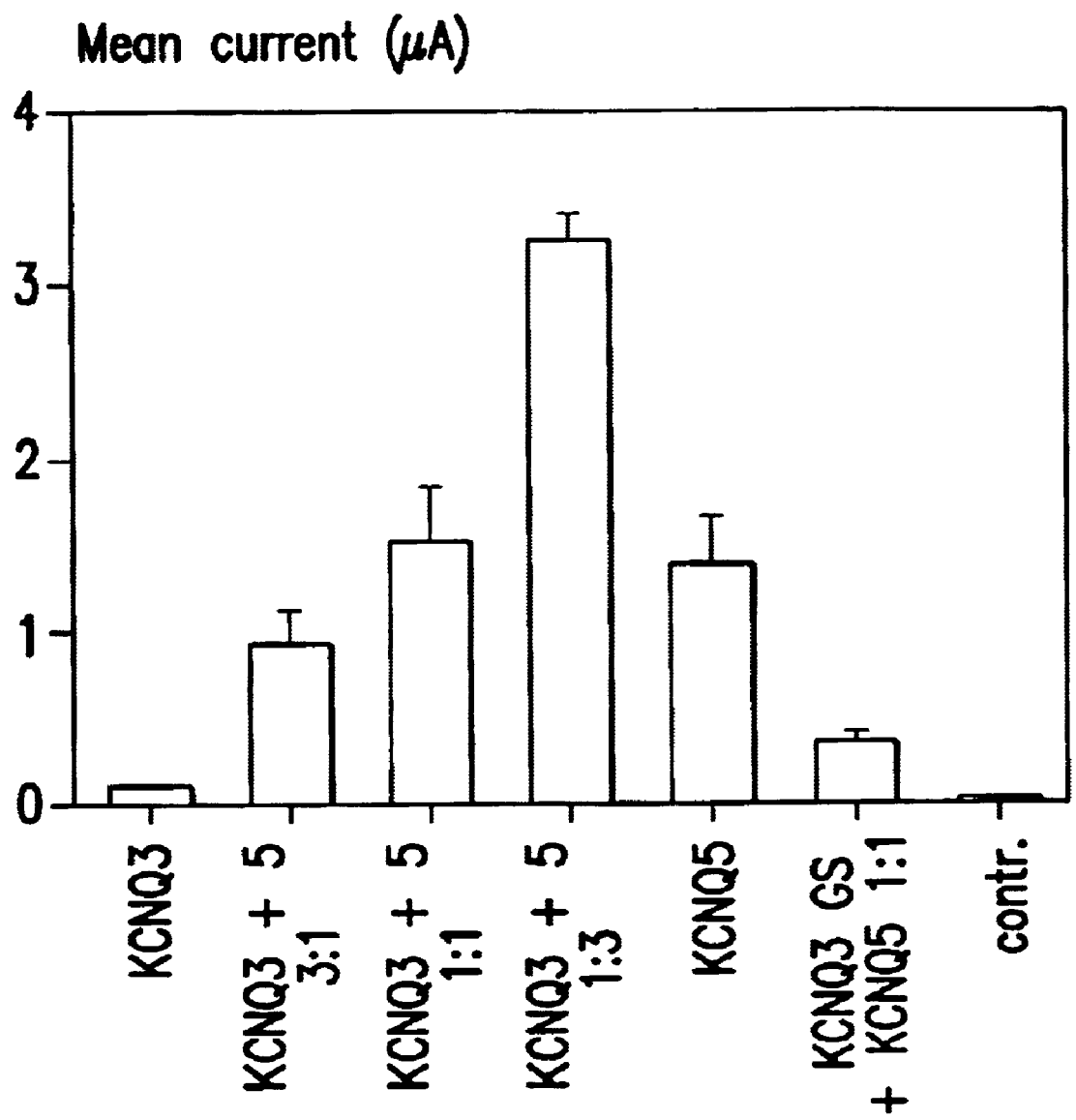

(6A) currents before stimulating the M1 receptor;

(6B) current observed 3 minutes after applying 10 $\mu$M muscarine. The pulse protocol is shown in the inset of panel b. No effect of 10 $\mu$M muscarine or oxotremorine methiodide was found in oocytes injected with KCNQ5 alone; and FIGS. 7A–C show the interactions between KCNQ2 and KCNQ5 (7A, 7B) and KCNQ3 and KCNQ5 (7C):

(7A) currents at the end of a two second pulse to 0 mV from a holding potential of −80 mV of oocytes injected with different combinations of KCNQ cRNAs (always 10 ng total amount of RNA). The current amplitude elicited by co-injecting KCNQ2 and KCNQ5 could be explained by a linear superposition of currents. Co-injection of KCNQ5 with the dominant negative mutant KCNQ2(G279S) or of KCNQ2 with the equivalent mutant KCNQ5(G278S) lead to a roughly 50% reduction in current amplitude, which is consistent with a lack of interaction since only 50% of WT cRNA was injected;

(7B) normalized current traces of experiments used for panel (A). Currents elicited by the depolarizing pulse to 0 mV are shown. KCNQ2 (labeled Q2) activates faster than KCNQ5 (Q5), and the co-expression of both yielded currents that may be explained by a linear superposition. Co-injecting KCNQ2 with the dominant negative (and otherwise non-functional) mutant KCNQ5(G278S) yielded currents that were kinetically similar to KCNQ2, and currents from a KCNQ5/KCNQ2(G279S) co-injection resembled KCNQ5 currents;

(7C), interactions between KCNQ3 and KCNQ5 measured as in panel (a). KCNQ3 yields only very small currents in Xenopus oocytes. Currents were enlarged when KCNQ5 was co-expressed with small amounts of KCNQ3, and reduced when co-expressed with larger amounts. The dominant negative mutant KCNQ3(G318S) decreased currents significantly below 50% of WT KCNQ5 currents that would be expected from the injected 50% of WT KCNQ5 cRNA in this experiment.

EXAMPLES

The invention is further illustrated with reference to the following examples which are not intended to be in any way limiting to the scope of the invention as claimed.

Example 1

Cloning and Characterisation of KCNQ5 cDNA

Using a near full-length KCNQ3 potassium channel CDNA as a probe, a human thalamus cDNA λGT11 phage library (Clontech, #HL5009b) was screened, and a partial cDNA clone encoding a protein fragment homologous to KCNQ potassium channels was isolated. It was distinct from the known members KCNQ1 (KvLQT1), KCNQ2, KCNQ3 and KCNQ4. We named the novel gene KCNQ5. Overlapping cDNA's containing the entire open reading frame were obtained by re-screening the cDNA library and by extending the 5' end in RACE (rapid amplification of cDNA ends) experiments using a Marathon kit (Clontech) with human brain cDNA. A complete CDNA was assembled and cloned into the oocyte expression vector PTLN [Lorenz C, Pusch M & Jentsch T J: Heteromultimeric CLC chloride channels with novel properties; *Proc. Natl. Acad. Sci. USA* 1996 93 13362–13366].

The cDNA encodes a polypeptide of 897 amino acids with a predicted mass of 99 kDa (SEQ ID NO: 2). Its overall amino-acid identity to KCNQ1, KCNQ2, KCNQ3 and KCNQ4 is 43%, 58%, 54%, and 61% respectively. Together with these proteins, it forms a distinct branch of the superfamily of voltage-gated potassium channels. As a typical member of this gene family, KCNQ5 has 6 predicted transmembrane domains and a P-loop between transmembrane domains S5 and S6. In potassium channels, which are tetramers of identical or homologous subunits, four of these highly conserved P-loops combine to form the ion-selective pore. As other KCNQ channels, KCNQ5 has a long predicted cytoplasmic carboxy terminus that accounts for about half of the protein. A conserved region present in the carboxy termini of KCNQ1, -2, -3 and -4 is also present in KCNQ5.

The sequence of KCNQ5 predicts several potential sites for phosphorylation by protein kinase C and one for protein kinase A. In contrast to KCNQ1 and KCNQ2, however, it lacks an amino terminal consensus site for cAMP-dependent phosphorylation.

A human multiple tissue Northern blot (Clontech, #7760–1) was probed with a cDNA fragment of KCNQ5. The fragment was labelled with $^{32}$P using the Rediprime labelling kit (Amersham). Hybridisation was performed in ExpressHyb solution according to the instructions of the manufacturer (Clontech). The filter was then exposed to Kodak BioMax film for 4 days.

Northern analysis of KCNQ5 expression in human tissues revealed a band of ≈9 kb in brain.

Example 2

Functional Expression of KCNQ5 Potassium Channel Subunits

KCNQ5 was expressed in Xenopus oocytes and its activity was investigated by two-electrode voltage clamping.

After linearization of the KCNQ5-containing pTLN vector with HpaI, capped cRNA was transcribed in vitro using the mMessage mMachine cRNA synthesis kit (Ambion). Usually 5–15 ng of cRNA were injected into Xenopus oocytes previously isolated by manual defolliculation and short collagenase treatment. In co-expression experiments cRNAs were injected at a 1:1 ratio. Oocytes were kept at 17° C. in modified Barth's solution (90 mM NaCl, 1 mM KCl, 0.41 mM CaCl$_2$, 0.33 mM Ca(NO$_3$)$_2$, 0.82 mM MgSO$_4$, 10 mM HEPES, 100 U penicillin—100 μg streptomycin/ml, pH 7.6).

Standard two-electrode voltage-clamp measurements were performed at room temperature 24 days after injection using a Turbotec 05 amplifier (npi instruments, Tamm, Germany) and pClamp 5.5 software (Axon Instruments). Currents were usually recorded in ND98 solution (see Table 2). Linopirdine (RBI, Natick, MA) was prepared as a 100 mM stock solution in DMSO and added to a final concentration of 200 μM to ND98.

TABLE 2

| Solution contents (Concentrations in mM) | | | | |
|---|---|---|---|---|
| ND98 | ND 100 | KD100 | Rb100 | Cs100 |
| 98 NaCl | 100 NaCl | 100 KCl | 100 RbCl | 100 CsCl |
| 2 KCl | | | | |
| 0.2 CaCl$_2$ | 0.2 CaCl$_2$ | 0.2 CaCl$_2$ | 0.2 CaCl$_2$ | 0.2 CaCl$_2$ |
| 2.8 MgCl$_2$ | 2.8 MgCl$_2$ | 2.8 MgCl$_2$ | 2.8 MgCl$_2$ | 2.8 MgCl$_2$ |

5 mM HEPES, pH 7.4

To determine the voltage dependence of apparent open probability, oocytes were clamped for 2 seconds to values between −80 mV to +40 mV, in 10 mV steps, followed by a constant −30 mV test pulse. Tail currents extrapolated to t=0 were obtained from a mono-exponential fit, normalised to the value at 0 mV and used for the analysis of apparent $P_{open}$. Data analysis used PClamp6 and Microcal Origin 5.0.

Figure 1:
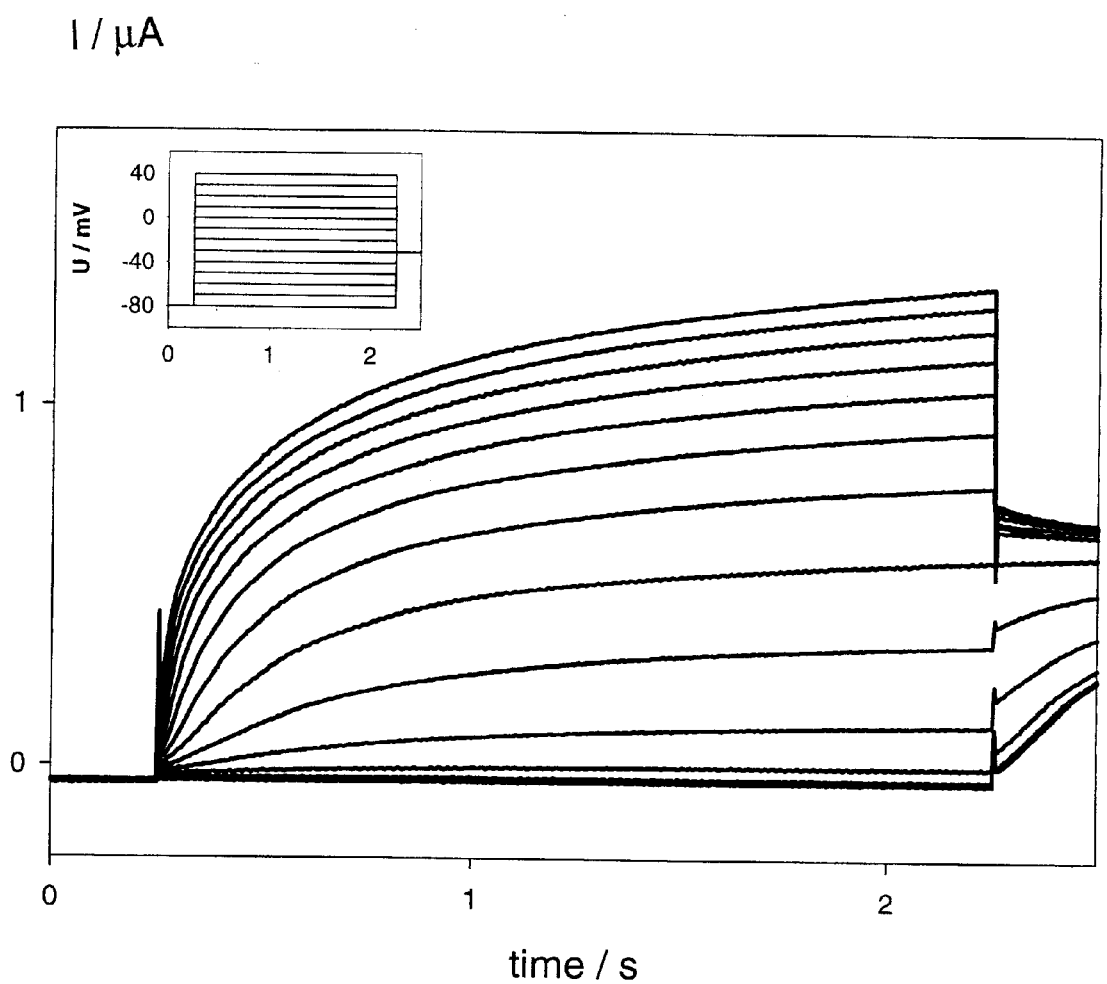
FIG. 1 shows the electrophysiological properties of KCNQ5 currents [1/$\mu$A vs. time/seconds]. Two-electrode voltage-clamp current traces from a Xenopus oocyte injected with KCNQ5 cRNA. Starting from a holding potential of −80 mV, cells were clamped for 2 seconds to voltages between −80 and +40 mV, in +10 mV steps, followed by a constant test pulse to −30 mV.

Similar to KCNQ1, KCNQ2, KCNQ3, and KCNQ4 also KCNQ5 yielded 30 currents that activated upon depolarisation (FIG. 1). Compared to KCNQ1, KCNQ2 and KCNQ2/3 channels, however, current activation was slower and occurred with a time constant in the order of 600 ms at +20mV (KCNQ2/KCNQ3 channels have a corresponding time constant of ≈300 ms). Deactivation of currents at physiological resting potentials (≈−30mV) was considerably faster (FIG. 1). Similar to KCNQ2, macroscopic currents often showed some inward rectification at positive potentials. KCNQ5 currents were inhibited by more than 80% by 5 mM $Ba^{++}$.

KCNQ1 assembles with minK (also known as KCNE1 or lsK) to form channels that yield larger currents and activate much slower. We therefore tested by co-expression whether minK affects KCNQ5 as well. At concentrations (1ng minK cRNA per oocyte) leading to drastic changes in KCNQ1 currents in parallel experiments, there was just a slight change in KCNQ5 currents.

Different KCNQ subunits can form heteromeric channels. Co-expression of KCNQ2 with KCNQ3, but not with KCNQ1, gave currents that were about tenfold larger than those from homomeric channels. Since also KCNQ2, KCNQ3 and KCNQ4 are expressed in the brain, we investigated whether these proteins interact functionally. Oocytes co-injected (at the same total cRNA concentration) with KCNQ2 and KCNQ5 cRNAs yielded currents that seemed not different from a linear superposition of currents from the respective homomeric channels.

Figure 2:
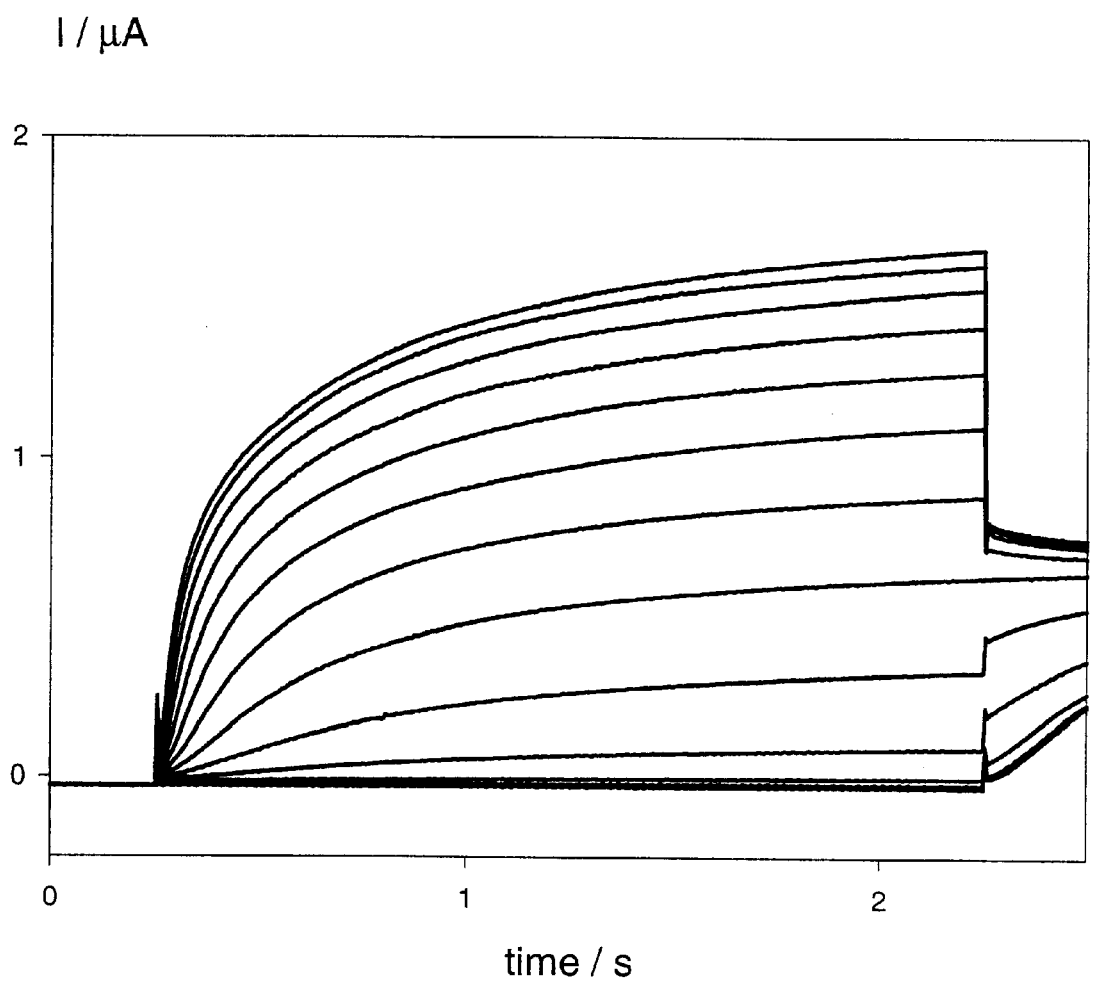
FIG. 2 shows the electrophysiological properties of currents arising from the co-expression of KCNQ5 with KCNQ3 [1/$\mu$A vs. time/seconds]. Starting from a holding potential of −80 mV cells were clamped for 2 seconds to voltages between −80 and +40 mV, in +10 mV steps, followed by a constant test pulse to −30 mV.
Figure 3:
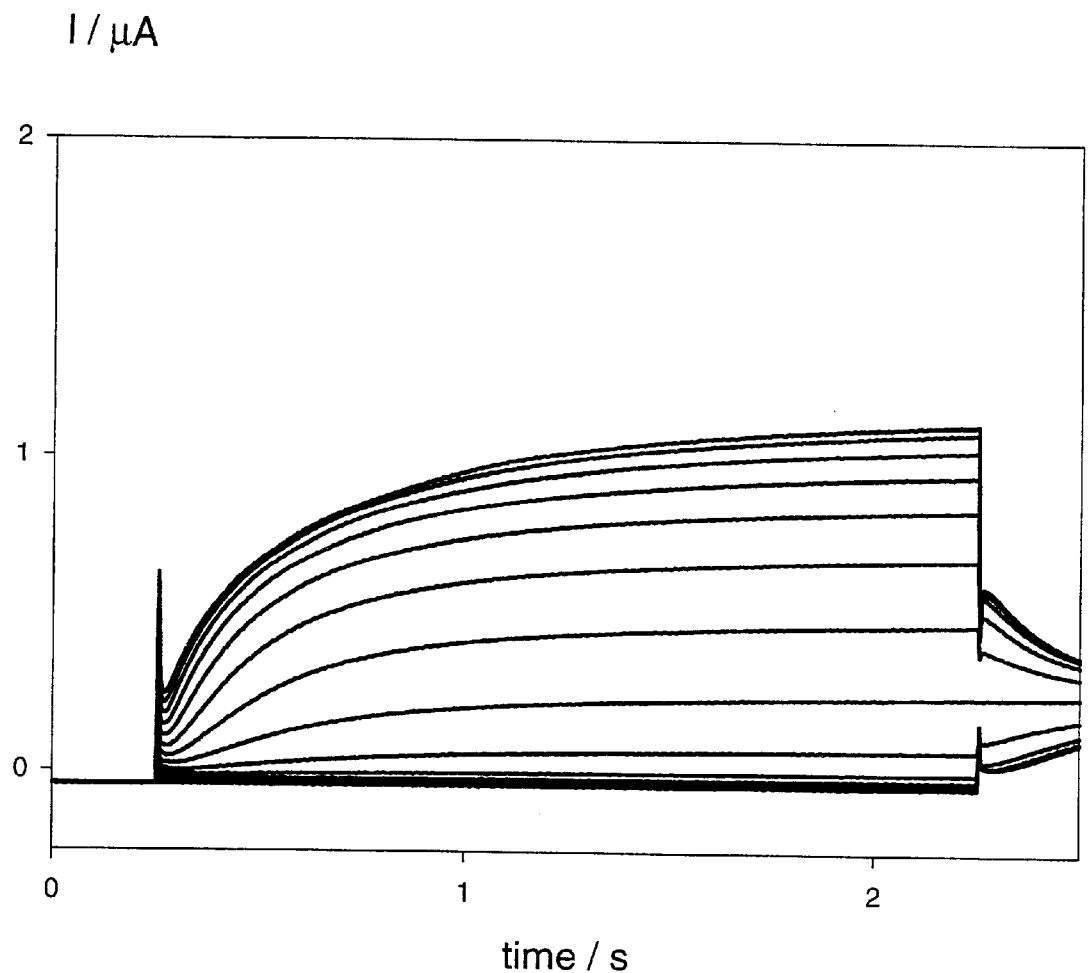
FIG. 3 shows the electrophysiological properties of currents arising from the co-expression of KCNQ5 with KCNQ4 (2B) [1/pA vs. time/seconds]. Starting from a holding potential of −80 mV cells were clamped for 2 seconds to voltages between −80 and +40 mV, in +10 mV steps, followed by a constant test pulse to −30 mV.
Figure 4A:
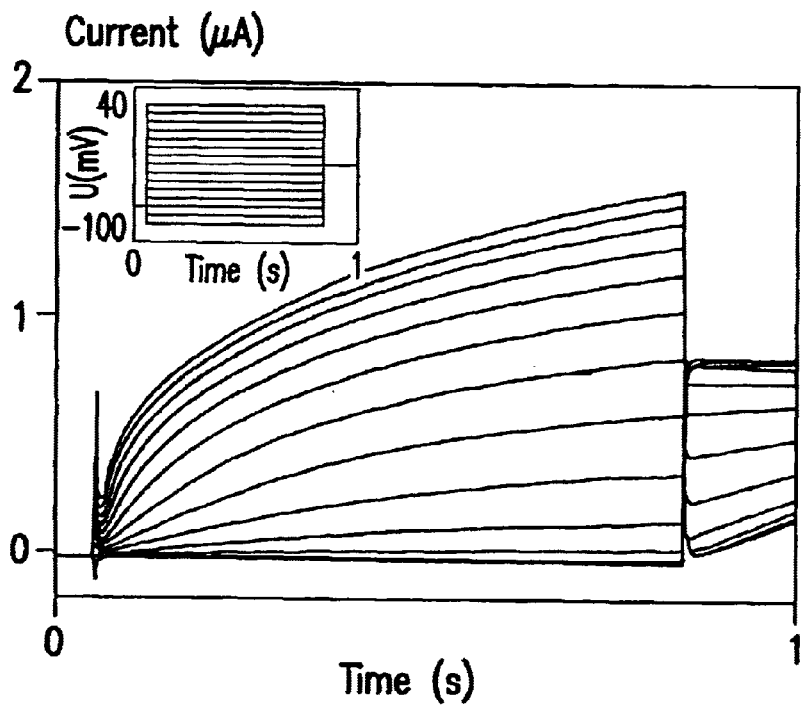
FIGS. 4A–G show the electrophysiological properties of KCNQ5. Both the splice variant I (found in brain) and splice variant III (found in muscle) were expressed in Xenopus oocytes and examined by two-electrode voltage clamping. Both variants activate slowly upon depolarisation, but form I (4A) initially activates slower than the muscle form III (4B). Starting from a holding potential of −80 mV, the voltage was stepped for 0.8 seconds to values between −100 and +40 mV in steps of 10 mV, followed by a voltage step to −30 mV (see inset, panel A). Channel activation by depolarization was fitted (for 2 sec. steps) by a sum of three exponential functions. For a step to +20 mV, the rate constants were $\hat{o}_1$=37. 2±2.2 ms, $\hat{o}_2$=246±17 m and $\hat{o}_3$= 1112±91 ms for splice variant I, while these constants were $\hat{o}_1$=24.5±0.8 ms, $\hat{o}_2$=163±6 ms, and $\hat{o}_3$=1690±46 ms (±SEM, n=16). This difference in kinetics also results in different curves when a typical M-current protocol is used (4C, variant I; 4D, variant III). Variant I induces currents that kinetically resemble M-currents. In this protocol, the membrane voltage is clamped for 1 second to voltages between −30 and −90 mV in steps of −10 mV, from a holding potential of −30 mV. This was followed by a step to −30 mV (panel C, inset). (4E, 4F), apparent open probabilities of variants I (4E) and variant III (4F) as a function of voltage obtained from tail current analysis as described in Methods. Mean values obtained from 12 oocytes are shown. Fitting a Boltzmann equation yielded $V_{1/2}$=−46±1 mV and an apparent gating charge of z=2.8±0.1 for isoform I, and $V_{1/2}$=−48±1 mV and an apparent gating charge of z=2.5±0.1 for isoform III. For this fit, values at potentials more positive than +10 mV were excluded, as these are probably affected by a second (inactivation) gating process which leads to a decrease of apparent $P_{open}$ at more positive potentials. (4G), ion selectivity of KCNQ5 currents (variant I). Extracellular sodium was replaced by equimolar amounts of potassium. The reversal potential is shown as a function of the potassium concentration. This yielded a slope of 51 mV/decade potassium concentration, indicating a highly selective potassium channel. Data are from 10 oocytes from 2 different batches.
Figure 4B:
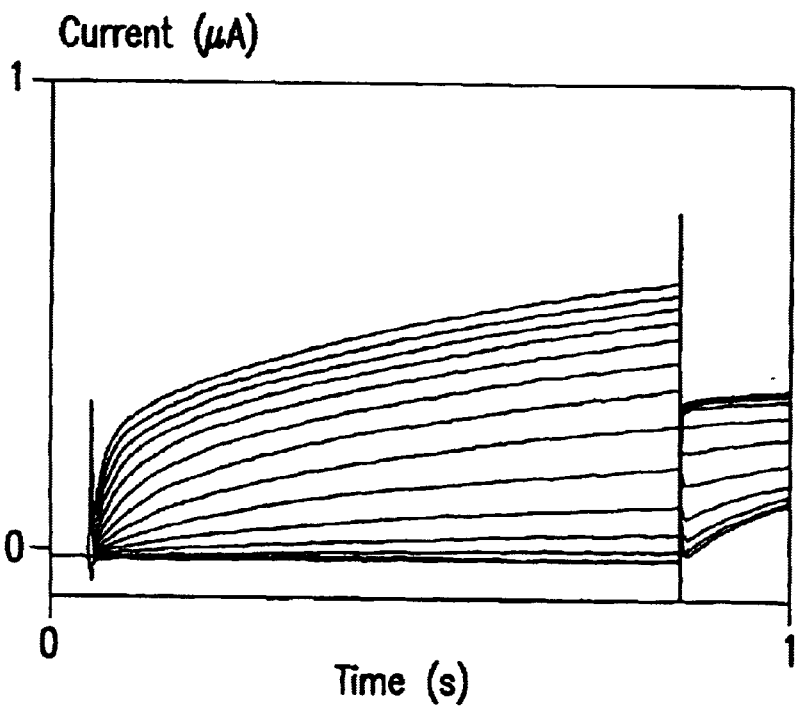
Figure 4C:
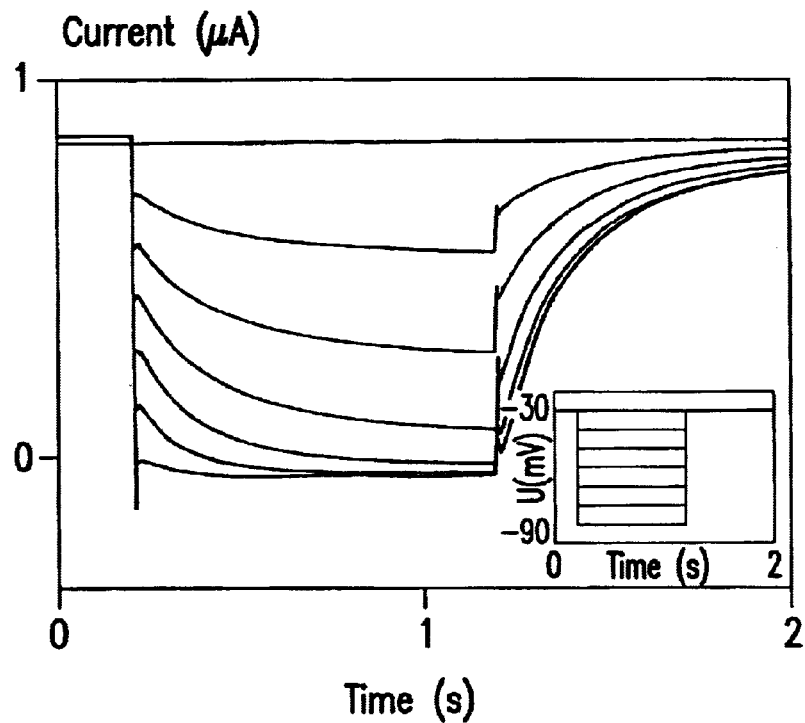
Figure 4D:
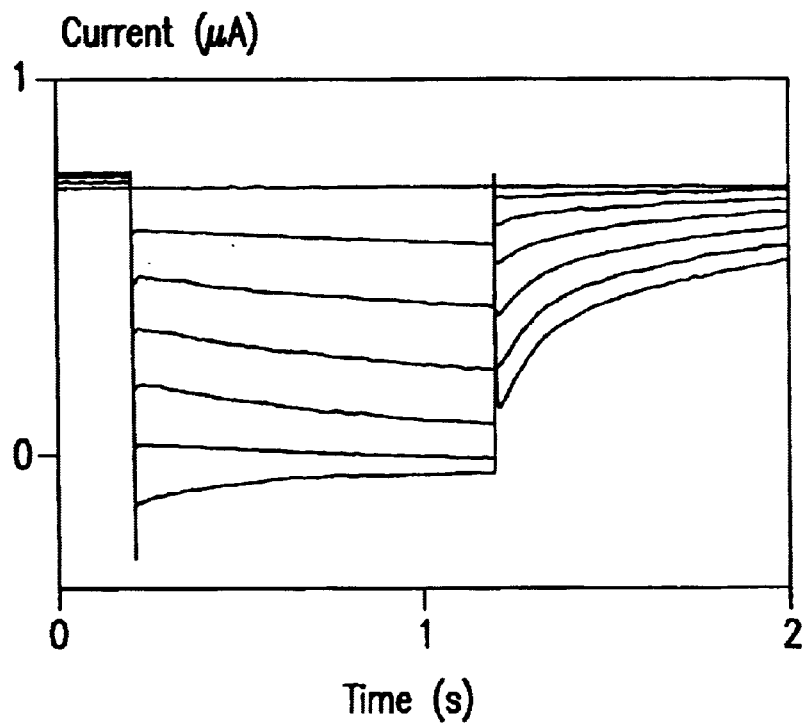
Figure 4G:
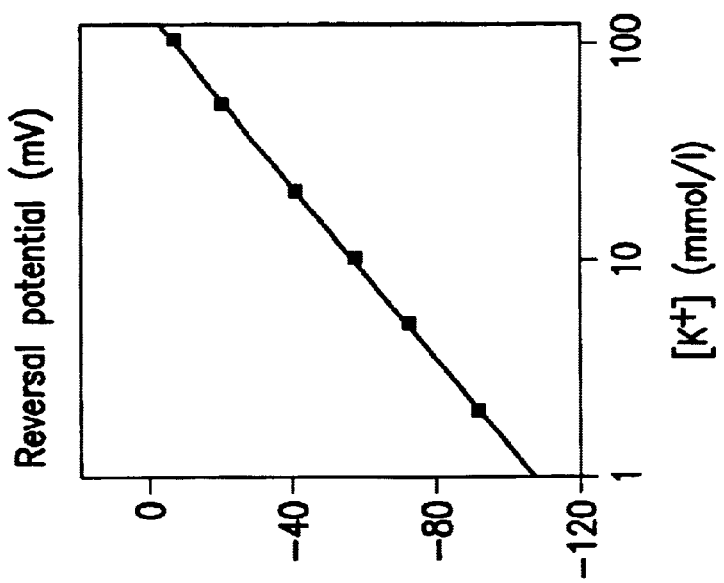
Figure 4F:
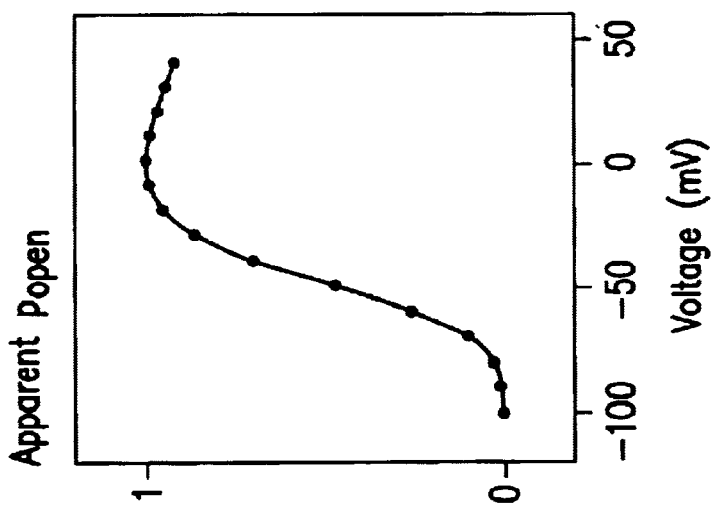
Figure 4E:
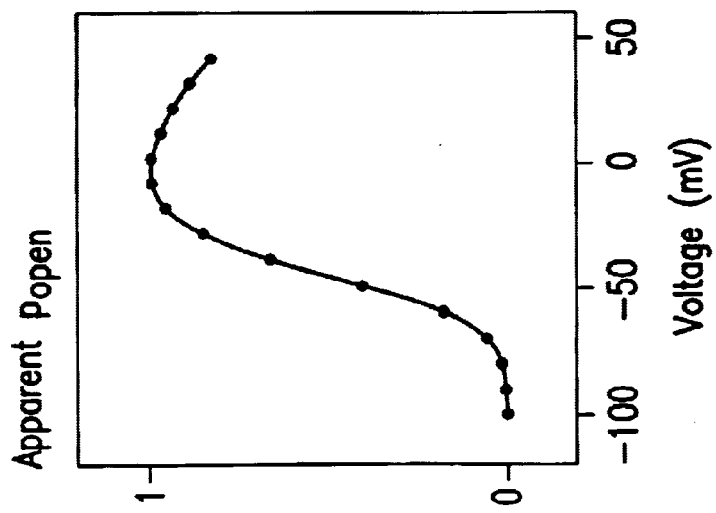
Figure 5A:
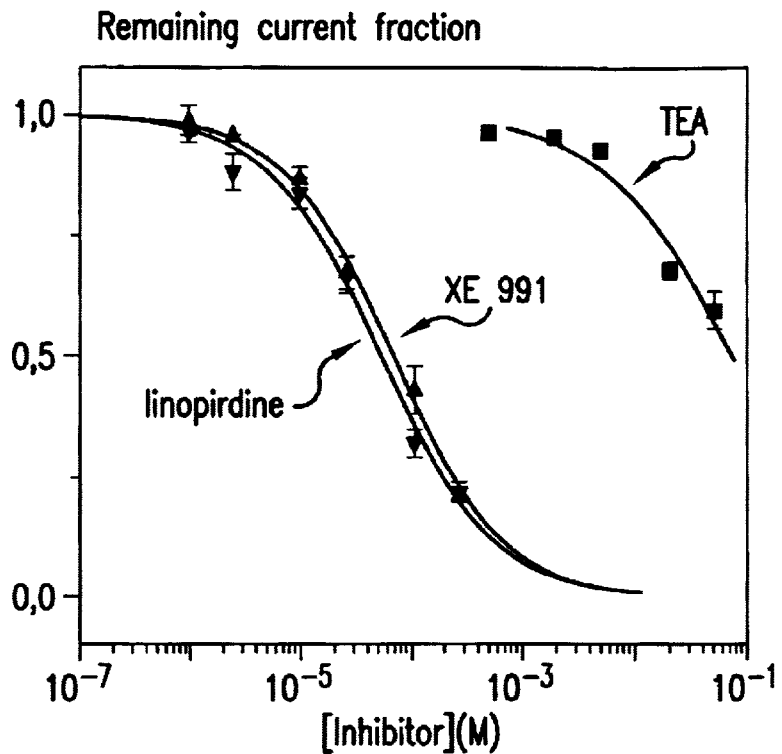
FIGS. 5A–C show the pharmacology of KCNQ5 and KCNQ3/5 heteromers. (5A) Inhibition of KCNQ5 homomers by extracellular linopirdine (down triangles), XE991 (up triangles) and TEA (squares). $IC_{50}$ values of 51±5 $\mu$M, 65±4 $\mu$M and 71±17 mM, respectively, were obtained from the plotted fit curves. (5B) Niflumic acid alters the voltage dependence of the apparent $P_{open}$. In the presence of 500 $\mu$M niflumic acid (open circles), the voltage dependence is shifted about 20 mV towards negative potentials. (5C) TEA sensitivity is altered in KCNQ3/5 heteromers. Coexpression of KCNQ5 and KCNQ3 (1:1) (diamonds) increased the $IC_{50}$ value to ~200 mM, coexpression with the KCNQ3 (T323Y) mutant (circles) decreased the $IC_{50}$ to ~30 mM. Data points in panels A and C are the means ±SEM of 4 to 12 individual measurements. $P_{open}$ was determined as in FIG. 3.
Figure 5B:
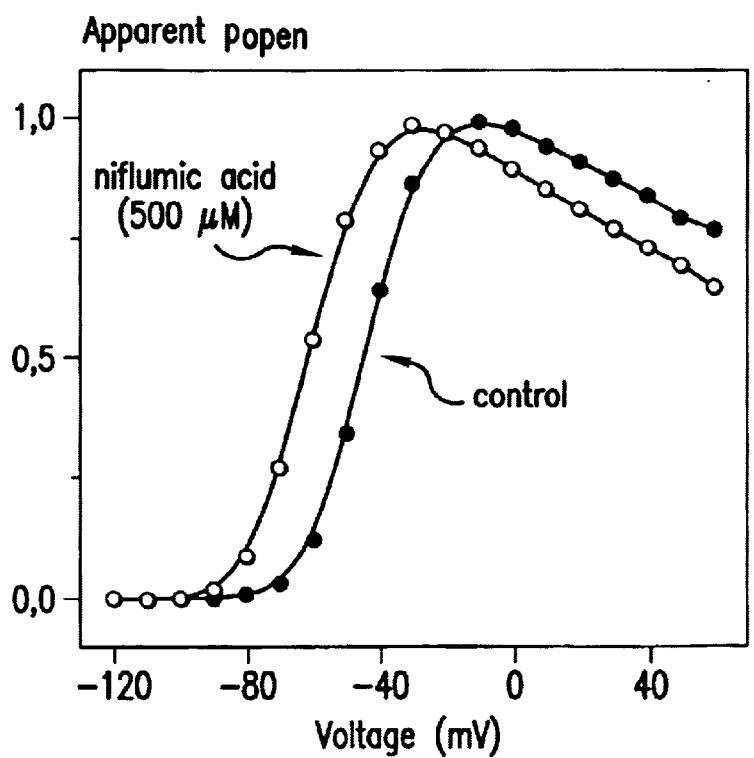
Figure 5C:
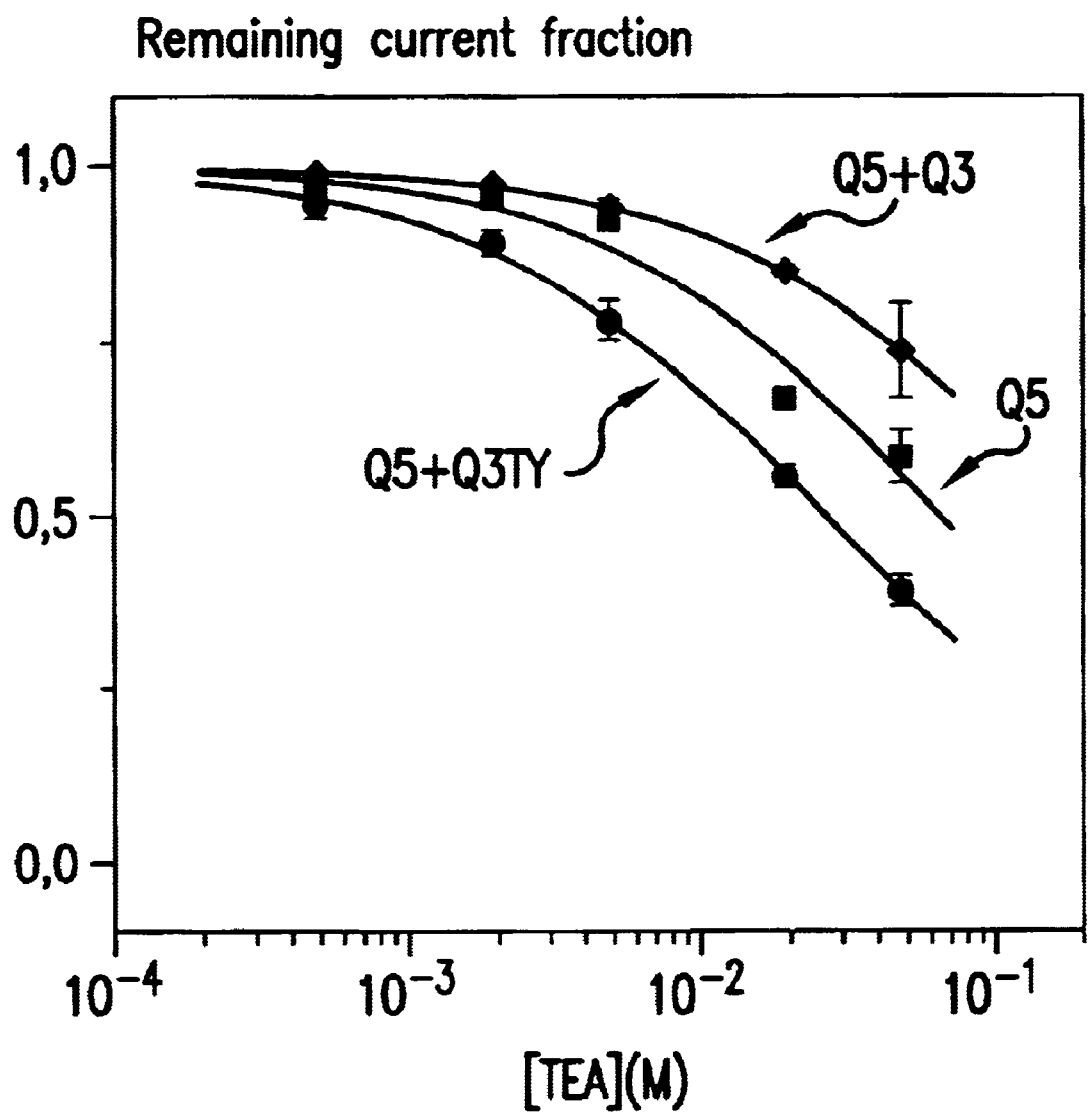
Figure 6A:
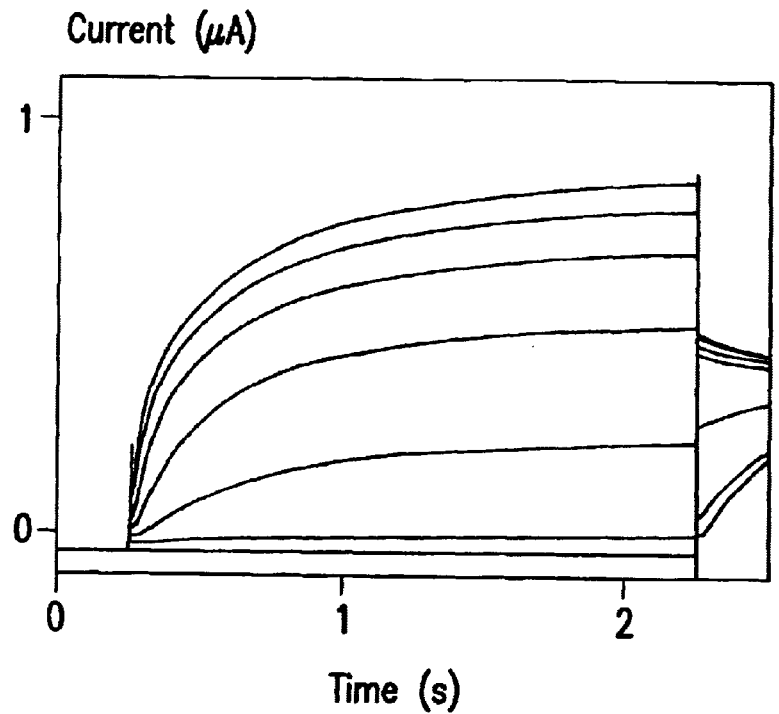
FIG. 6 shows the inhibition of KCNQ5 currents by stimulating M1 receptors which were co-expressed in Xenopus oocytes.
Figure 6B:
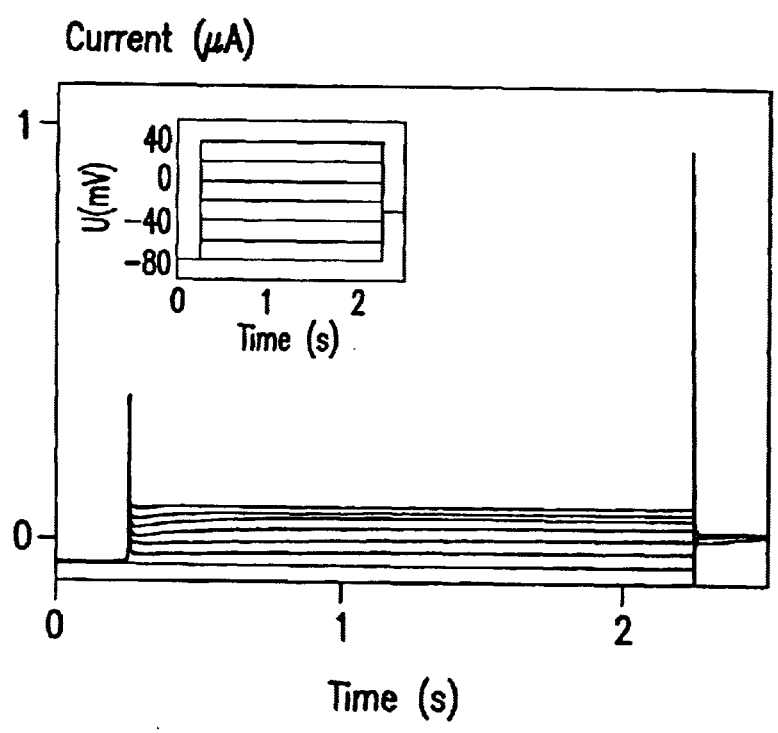

By contrast, co-expression of KCNQ3 with KCNQ5 yielded currents that were significantly larger than could be explained by a superposition of currents from the respective homomeric channels (FIGS. 2A). Further, co-expression of KCNQ5 and KCNQ4 decreased currents when compared to homomeric channels (FIG. 2B).

Linopirdine, a potent and rather specific inhibitor for M-currents, nearly completely inhibits KCNQ2/KCNQ3 channels at a concentration of 200 $\mu$M.

This concentration of Linopirdine inhibited KCNQ5 by about 80%.

What is claimed is:

1. An isolated nucleic acid molecule comprising SEQ ID NO: 1.

2. The isolated polynucleotide according to claim 1, wherein said polynucleotide is a cloned polynucleotide.

3. The isolated polynucleotide according to claim 2, wherein the polynucleotide is cloned or produced from a cDNA library.

4. The isolated polynucleotide according to claim 1, wherein said polynucleotide encodes a potassium channel subunit.

5. The isolated polynucleotide according to claims 4, encoding the KCNQ5 potassium channel subunit having the amino acid sequence represented by SEQ ID NO: 2.

6. A vector construct comprising the polynucleotide according to claim 1.

7. A cell comprising the polynucleotide according to claim 1.

8. The cell according to claim 7 genetically manipulated by the incorporation of a KCNQ5 channel subunit having the amino acid sequence presented as SEQ ID NO: 2.

9. The cell according to claim 7, genetically manipulated to co-express one or more KCNQ channel subunits.

10. The cell according to claim 9, genetically manipulated to co-express

KCNQ5 and KCNQ1 channel subunits;
KCNQ5 and KCNQ2 channel subunits;
KCNQ5 and KCNQ3 channel subunits;
KCNQ5 and KCNQ4 channel subunits;
KCNQ5 and KCNQ1 and KCNQ2 channel subunits;
KCNQ5 and KCNQ1 and KCNQ3 channel subunits;
KCNQ5 and KCNQ1 and KCNQ4 channel subunits;
KCNQ5 and KCNQ2 and KCNQ3 channel subunits;
KCNQ5 and KCNQ2 and KCNQ4 channel subunits;
KCNQ5 and KCNQ3 and KCNQ4 channel subunits;
KCNQ5 and KCNQ1 and KCNQ2 and KCNQ3 channel subunits;
KCNQ5 and KCNQ1 and KCNQ2 and KCNQ4 channel subunits;
KCNQ5 and KCNQ1 and KCNQ3 and KCNQ4 channel subunits, or
KCNQ5 and KCNQ2 and KCNQ3 and KCNQ4 channel subunits.

11. The cell according to claim 9, genetically manipulated to co-express KCNQ2 and KCNQ5 channel subunits to KCNQ3 and KCNQ5 channel subunits together.

12. The cell according to claim 7, wherein said cell is an eukaryotic cell.

13. The cell according to claim 12, wherein said eukaryotic cell is selected from the group consisting of a human embryonic kidney (HEK) cell, a HEK 293 cell, a BHK21 cell, a Chinese hamster ovary (CHO) cell, a *Xenopus laevis* (XLO) cell, and a COS cell.

14. An isolated membrane preparation derived from a cell according to claim 7.

15. A method for obtaining a substantially homogeneous source of a human potassium channel, comprising a KCNQ5 subunit, which method comprises the steps of:

culturing a cellular host having incorporated expressibly therein a polynucleotide according to claim 1, and recovering the cultured cells.

16. The isolated nucleic acid molecule of claim 1, wherein said nucleic acid molecule encodes a human, rat or murine KCNQ5 protein having the amino acid sequence of SEQ ID NO: 2.

17. A cell comprising the vector construct according to claim 6.

18. The cell according to claim 12, wherein said eukaryotic cell is selected from the group consisting of a mammalian cell, an oocyte, and a yeast cell.

19. A method for obtaining a substantially homogeneous source of a human potassium channel, comprising a KCNQ5 subunit, which method comprises the steps of:

culturing a cellular host having incorporated expressibly therein the vector construct according to claim 6, and recovering the cultured cells.

* * * * *